US012173040B2

(12) United States Patent
Zamora et al.

(10) Patent No.: US 12,173,040 B2
(45) Date of Patent: Dec. 24, 2024

(54) COMPOSITION AND METHOD FOR DELIVERY OF BMP-2 AMPLIFIER/CO-ACTIVATOR FOR ENHANCEMENT OF OSTEOGENESIS

(71) Applicants: Ferring B.V., Hoofddorp (NL); Brookhaven Science Associates, LLC, Upton, NY (US)

(72) Inventors: Paul O. Zamora, Gaithersburg, MD (US); Brent Lee Atkinson, Highlands Ranch, CO (US); Xinhua Lin, Plainview, NY (US); Louis A. Pena, Poquott, NY (US)

(73) Assignees: Ferring B.V., Hoofddorp (NL); Brookhaven Science Associates, LLC

( * ) Notice: Subject to any disclaimer, the term of this patent is extended or adjusted under 35 U.S.C. 154(b) by 0 days.

(21) Appl. No.: 17/443,012

(22) Filed: Jul. 19, 2021

(65) Prior Publication Data
US 2021/0347838 A1 Nov. 11, 2021

Related U.S. Application Data

(60) Continuation of application No. 16/358,343, filed on Mar. 19, 2019, now Pat. No. 11,078,244, which is a division of application No. 14/452,304, filed on Aug. 5, 2014, now Pat. No. 10,246,499, which is a continuation of application No. 13/186,165, filed on Jul. 19, 2011, now Pat. No. 8,796,212, which is a division of application No. 11/767,391, filed on Jun. 22, 2007, now Pat. No. 7,981,862.

(60) Provisional application No. 60/805,594, filed on Jun. 22, 2006.

(51) Int. Cl.
| | |
|---|---|
| A61K 38/18 | (2006.01) |
| A61L 27/12 | (2006.01) |
| A61L 27/16 | (2006.01) |
| A61L 27/22 | (2006.01) |
| A61L 27/24 | (2006.01) |
| A61L 27/34 | (2006.01) |
| A61L 27/50 | (2006.01) |
| C07K 14/47 | (2006.01) |
| C07K 14/51 | (2006.01) |

(52) U.S. Cl.
CPC ...... *C07K 14/4705* (2013.01); *A61K 38/1875* (2013.01); *A61L 27/12* (2013.01); *A61L 27/16* (2013.01); *A61L 27/22* (2013.01); *A61L 27/227* (2013.01); *A61L 27/24* (2013.01); *A61L 27/34* (2013.01); *A61L 27/507* (2013.01); *C07K 14/51* (2013.01); *A61L 2430/02* (2013.01)

(58) Field of Classification Search
CPC ......... A61K 38/18; C07K 14/51; C07K 14/47
See application file for complete search history.

(56) References Cited

U.S. PATENT DOCUMENTS

| | | |
|---|---|---|
| 3,272,204 A | 9/1966 | Artandi |
| 4,172,128 A | 10/1979 | Thiele et al. |
| 4,193,138 A | 3/1980 | Okita |
| 4,563,350 A | 1/1986 | Nathan et al. |
| 4,747,848 A | 5/1988 | Maini |
| 4,842,575 A | 6/1989 | Hoffman, Jr. et al. |
| 5,108,436 A | 4/1992 | Chu et al. |
| 5,197,977 A | 3/1993 | Hoffman, Jr. et al. |
| 5,202,311 A | 4/1993 | Folkman et al. |
| 5,326,695 A | 7/1994 | Andersson et al. |
| 5,509,899 A | 4/1996 | Fan et al. |
| 5,510,418 A | 4/1996 | Rhee et al. |
| 5,512,545 A | 4/1996 | Brown et al. |
| 5,563,046 A | 10/1996 | Mascarenhas et al. |
| 5,608,035 A | 3/1997 | Yanofsky et al. |
| 5,635,597 A | 6/1997 | Barrett et al. |
| 5,643,873 A | 7/1997 | Barrett et al. |
| 5,648,458 A | 7/1997 | Cwirla et al. |
| 5,650,234 A | 7/1997 | Dolence et al. |
| 5,654,276 A | 8/1997 | Barrett et al. |
| 5,665,114 A | 9/1997 | Weadock et al. |
| 5,668,110 A | 9/1997 | Barrett et al. |
| 5,674,977 A | 10/1997 | Gariepy |
| 5,679,637 A | 10/1997 | Lapp' et al. |
| 5,679,673 A | 10/1997 | Bowen et al. |
| 5,684,136 A | 11/1997 | Godowski |
| 5,728,802 A | 3/1998 | Barrett et al. |
| 5,759,515 A | 6/1998 | Rhodes et al. |
| 5,767,234 A | 6/1998 | Yanofsky et al. |
| 5,770,704 A | 6/1998 | Godowski |

(Continued)

FOREIGN PATENT DOCUMENTS

| | | |
|---|---|---|
| WO | WO-200018921 A2 | 4/2000 |
| WO | WO-200064481 A1 | 11/2000 |

(Continued)

OTHER PUBLICATIONS

Hsu et al., Proc. Nat'l. Acad. Sci. USA, 1999, vol. 96(7):3540-3545.*
Patel et al., J. Mater. Sci.: Mater. Med., May 2005, vol. 16, 429-440.*
Aaronson et al., "Human KGF is FGF-related with Properties of a Paracrine Effector of Epithelial Cell Growth", Science vol. 245 No. 4919, 1989, 752-755.
Aaronson et al., "Keratinocyte Growth Factor. A Fibroblast Growth Factor Family Member with Unusual Target Cell Specificity", Annals NY Acad. Sci. vol. 638, 1991, 62-77.

(Continued)

*Primary Examiner* — Xiaozhen Xie
(74) *Attorney, Agent, or Firm* — Foley & Lardner LLP

(57) ABSTRACT

A composition comprising a synthetic growth factor analogue comprising a non-growth factor heparin binding region, a linker and a sequence that binds specifically to a cell surface receptor and an osteoconductive material where the synthetic growth factor analogue is attached to and can be released from the osteoconductive material and is an amplifier/co-activator of osteoinduction.

19 Claims, 5 Drawing Sheets

Specification includes a Sequence Listing.

(56) References Cited

U.S. PATENT DOCUMENTS

| | | |
|---|---|---|
| 5,773,569 A | 6/1998 | Wrighton et al. |
| 5,786,322 A | 7/1998 | Barrett et al. |
| 5,786,331 A | 7/1998 | Barrett et al. |
| 5,789,182 A | 8/1998 | Yayon et al. |
| 5,830,851 A | 11/1998 | Wrighton et al. |
| 5,830,995 A | 11/1998 | Shoyab et al. |
| 5,854,207 A | 12/1998 | Lee et al. |
| 5,861,476 A | 1/1999 | Barrett et al. |
| 5,866,113 A | 2/1999 | Hendriks et al. |
| 5,869,451 A | 2/1999 | Dower et al. |
| 5,880,096 A | 3/1999 | Barrett et al. |
| 5,902,799 A | 5/1999 | Herrmann et al. |
| 5,916,585 A | 6/1999 | Cook et al. |
| 5,932,462 A | 8/1999 | Harris et al. |
| 5,945,457 A | 8/1999 | Plate et al. |
| 5,952,474 A | 9/1999 | Kayman et al. |
| 5,955,588 A | 9/1999 | Tsang et al. |
| 5,965,532 A | 10/1999 | Bachovchin |
| 5,989,866 A | 11/1999 | Deisher et al. |
| 5,994,104 A | 11/1999 | Anderson et al. |
| 6,001,364 A | 12/1999 | Rose et al. |
| 6,011,002 A | 1/2000 | Pastan et al. |
| 6,030,812 A | 2/2000 | Bauer et al. |
| 6,051,648 A | 4/2000 | Rhee et al. |
| 6,096,798 A | 8/2000 | Luthra et al. |
| 6,099,562 A | 8/2000 | Ding et al. |
| 6,102,932 A | 8/2000 | Kurz |
| 6,113,629 A | 9/2000 | Ken |
| 6,120,904 A | 9/2000 | Hostettler et al. |
| 6,121,236 A | 9/2000 | Ben-Sasson |
| 6,136,015 A | 10/2000 | Kurz et al. |
| 6,159,165 A | 12/2000 | Ferrera et al. |
| 6,165,194 A | 12/2000 | Denardo |
| 6,168,615 B1 | 1/2001 | Ken et al. |
| 6,168,784 B1 | 1/2001 | Offord et al. |
| 6,171,326 B1 | 1/2001 | Ferrera et al. |
| 6,174,530 B1 | 1/2001 | Rose et al. |
| 6,174,721 B1 | 1/2001 | Innis |
| 6,214,795 B1 | 4/2001 | Benjamin et al. |
| 6,217,873 B1 | 4/2001 | Rose et al. |
| 6,221,066 B1 | 4/2001 | Ferrera et al. |
| 6,231,600 B1 | 5/2001 | Zhong |
| 6,231,892 B1 | 5/2001 | Hubbell et al. |
| 6,235,716 B1 | 5/2001 | Ben-Sasson |
| 6,248,057 B1 | 6/2001 | Mavity et al. |
| 6,251,864 B1 | 6/2001 | Dower et al. |
| 6,258,371 B1 | 7/2001 | Koulik et al. |
| 6,270,788 B1 | 8/2001 | Koulik et al. |
| 6,284,503 B1 | 9/2001 | Caldwell et al. |
| 6,294,359 B1 | 9/2001 | Fiddes et al. |
| 6,306,153 B1 | 10/2001 | Kurz et al. |
| 6,306,165 B1 | 10/2001 | Patnaik et al. |
| 6,309,660 B1 | 10/2001 | Hsu et al. |
| 6,323,323 B1 | 11/2001 | Sledziewski et al. |
| 6,326,468 B1 | 12/2001 | Canne et al. |
| 6,342,591 B1 | 1/2002 | Zamora et al. |
| 6,350,731 B1 | 2/2002 | Jehanli et al. |
| 6,368,347 B1 | 4/2002 | Maini et al. |
| 6,377,349 B1 | 4/2002 | Fercher |
| 6,383,204 B1 | 5/2002 | Ferrero et al. |
| 6,387,978 B2 | 5/2002 | Ronan et al. |
| 6,406,687 B1 | 6/2002 | Luthra et al. |
| 6,410,044 B1 | 6/2002 | Chudzik et al. |
| 6,416,541 B2 | 7/2002 | Denardo et al. |
| 6,426,332 B1 | 7/2002 | Rueger et al. |
| 6,451,543 B1 | 9/2002 | Kochendoerfer et al. |
| 6,458,889 B1 | 10/2002 | Trollsas et al. |
| 6,491,965 B1 | 12/2002 | Berry et al. |
| 6,497,729 B1 | 12/2002 | Moussy et al. |
| 6,514,534 B1 | 2/2003 | Sawhney |
| 6,534,591 B2 | 3/2003 | Rhee et al. |
| 6,548,634 B1 | 4/2003 | Ballinger et al. |
| 6,551,305 B2 | 4/2003 | Ferrera et al. |
| 6,585,765 B1 | 7/2003 | Hossainy et al. |
| 6,596,699 B2 | 7/2003 | Zamora et al. |
| 6,616,617 B1 | 9/2003 | Ferrera et al. |
| 6,630,580 B2 | 10/2003 | Tsang et al. |
| 6,638,291 B1 | 10/2003 | Ferrera et al. |
| 6,656,201 B2 | 12/2003 | Ferrera et al. |
| 6,656,218 B1 | 12/2003 | Denardo et al. |
| 6,818,018 B1 | 11/2004 | Sawhney |
| 6,846,853 B2 | 1/2005 | Shimp |
| 6,863,899 B2 | 3/2005 | Koblish et al. |
| 6,866,155 B2 | 3/2005 | Nagel |
| 6,921,811 B2 | 7/2005 | Zamora et al. |
| 6,949,251 B2 | 9/2005 | Dalai et al. |
| 6,984,393 B2 | 1/2006 | Amsden |
| 7,025,990 B2 | 4/2006 | Sawhney |
| 7,041,641 B2 | 5/2006 | Rueger et al. |
| 7,166,574 B2 | 1/2007 | Pena et al. |
| 7,241,736 B2 | 7/2007 | Hunter et al. |
| 7,253,254 B1 | 8/2007 | Sebald |
| 7,414,028 B1 | 8/2008 | Zamora et al. |
| 7,468,210 B1 | 12/2008 | Zamora |
| 7,482,427 B2 | 1/2009 | Pena et al. |
| 7,528,105 B1 | 5/2009 | Pena et al. |
| 7,598,224 B2 | 10/2009 | Zamora et al. |
| 7,671,012 B2 | 3/2010 | Zamora et al. |
| 7,700,563 B2 | 4/2010 | Pena et al. |
| 7,820,172 B1 | 10/2010 | Zamora et al. |
| 7,981,862 B2 | 7/2011 | Zamora et al. |
| 8,101,570 B2 | 1/2012 | Takahashi et al. |
| 8,163,717 B2 | 4/2012 | Zamora et al. |
| 8,227,411 B2 | 7/2012 | Zamora et al. |
| 8,796,212 B2 | 8/2014 | Zamora et al. |
| 9,670,258 B2 | 6/2017 | Zamora |
| 10,246,499 B2 | 4/2019 | Zamora et al. |
| 2001/0014662 A1 | 8/2001 | Rueger et al. |
| 2002/0115836 A1 | 8/2002 | Tsang et al. |
| 2002/0160098 A1 | 10/2002 | Zamora et al. |
| 2003/0224996 A1 | 12/2003 | Opperman et al. |
| 2004/0002558 A1* | 1/2004 | Mckay ............... A61L 27/58 623/23.61 |
| 2004/0038348 A1* | 2/2004 | Pena ............... A61P 19/08 435/325 |
| 2004/0068266 A1 | 4/2004 | Delmotte |
| 2004/0087505 A1 | 5/2004 | Pena et al. |
| 2004/0151764 A1 | 8/2004 | Zamora |
| 2005/0196425 A1* | 9/2005 | Zamora ............... C07K 14/503 514/10.2 |
| 2005/0199156 A1 | 9/2005 | Khairoun et al. |
| 2005/0222394 A1 | 10/2005 | Zamora et al. |
| 2006/0024347 A1 | 2/2006 | Zamora et al. |
| 2006/0199764 A1 | 9/2006 | Zamora et al. |
| 2006/0205652 A1 | 9/2006 | Zamora et al. |
| 2008/0063622 A1 | 3/2008 | Zamora et al. |
| 2008/0160169 A1 | 7/2008 | Zamora et al. |
| 2008/0166392 A1 | 7/2008 | Zamora et al. |
| 2008/0227696 A1 | 9/2008 | Takahashi et al. |
| 2009/0111743 A1 | 4/2009 | Takahashi |
| 2009/0143566 A1 | 6/2009 | Zamora et al. |
| 2010/0267650 A1 | 10/2010 | Zamora et al. |
| 2010/0298218 A1 | 11/2010 | Takahashi et al. |
| 2011/0305741 A1 | 12/2011 | Zamora et al. |
| 2012/0202848 A1* | 8/2012 | Greene ............... A61P 1/04 546/171 |
| 2012/0309694 A1 | 12/2012 | Zamora et al. |
| 2013/0331328 A1* | 12/2013 | Byers ............... A61K 31/4406 546/280.4 |
| 2015/0353615 A9 | 12/2015 | Zamora |
| 2016/0376334 A1 | 12/2016 | Zamora |
| 2018/0100002 A1 | 4/2018 | Zamora |
| 2019/0322712 A1 | 10/2019 | Zamora et al. |

FOREIGN PATENT DOCUMENTS

| | | |
|---|---|---|
| WO | WO-200204015 A1 | 1/2002 |
| WO | WO-200210221 A1 | 2/2002 |
| WO | WO-200219963 A2 | 3/2002 |
| WO | WO-200220033 A1 | 3/2002 |

(56) References Cited

FOREIGN PATENT DOCUMENTS

| WO | WO-200262823 A2 | 8/2002 | |
|---|---|---|---|
| WO | WO-2004018499 A2 * | 3/2004 | ......... A61K 38/1709 |

OTHER PUBLICATIONS

Abraham et al., "Heparin-Binding EGF-like Growth Factor: Characterization of Rat and Mouse cDNA Clones, Protein Domain Conservation Across Species, and Transcript Expression in Tissues", Biochem. Biophys. Res. Commun. vol. 190 Issue 1, 1993, 125-133.
Ahmed et al., "Role of VEFGF Receptor-1 (Fit-1) in Mediating Calcium-Dependent Nitric Oxide Release and Limiting DNA Synthesis in Human Trophoblast Cells", Lab Invest, vol. 76(6), 1977, 779-791.
Akiyama et al., "Constitutively Active BMP Type I Receptors Transduce BMP-2 Signals without the Ligand in C2C12 Myoblasts", Exp. Cell. Res. vol. 235 No. 2, 1997, 362-369.
Andrades et al., "A Recombinant Human TGF-B1 Fusion Protein with Collagen-Binding Domain Promostes Migration, Growth, and Differentiation of Bone Marrow Mesenchymal Cells", Experimental Cell Research vol. 250, No. 2, 1999, 485-498.
Applicant Initiated Interview Summary dated Feb. 22, 2018 corresponding to U.S. Appl. No. 15/819,444.
Attisano et al., "Smads as Transcriptional Co-Modulators", Curr. Opin. Cell Biol. vol. 12 No. 2, 2000, 235-243.
Baird et al., "Receptor- and heparin-binding domains of basic fibroblast growth factor", Proc. Natl. Acad. Sci., vol. 85, 1988, 2324-2328.
Ballinger et al., "Semirational design of a potent, artificial agonist of fibroblast growth factor receptors", Nature Biotechnology vol. 17, 1999, 1199-1204.
Bates et al., "Biosynthesis of Human Fibroblast Growth Factor 5", Mol. Cell Biol., vol. 11 No. 4, 1991, 1840-1845.
Binetruy-Tournaire et al., "Identification of a Peptide Blocking Vascular Endothelial Growth Factor (VEGF)-mediated Angiogenesis", The EMBO Journal, vol. 19, No. 7, 2000, 1525-1533.
Blunt et al., "Overlapping Expression and Redundant Activation of Mesenchymal Fibroblast Growth Factor (FGF) Receptors by Alternatively Spliced FGF-8 Ligands", J. Bid. Chem. vol. 272 No. 6, 1997, 3733-3738.
Bork, Peer, "Go Hunting in Sequence Databases But Watch Out for Traps", Trends Genet., vol. 12 No. 10, Oct. 1996, 425-427.
Bork, Peer, "Powers and Pitfalls in Sequence Analysis: the 70% Hurdle", Genome Research vol. 10, 2000, 398-400.
Brennand, David M. et al., "Identification of a Cyclic Peptide Inhibitor of Platelet-Derived Growth Factor-BB Receptor-Binding and Mitogen-Induced DNA Synthesis in Human Fibroblasts", FEBS Letters, 413, 1997, 70-74.
Brenner, Steve, "Errors in Genome Annotation", Trends in Genetics vol. 15 No. 4, Apr. 1999, 132-133.
Burgess, Wilson H. et al., "The Heparin-Binding (Fibroblast) Growth Factor Family of Proteins", Ann. Rev. Biochem. vol. 58, 1989, 575-606.
Burkus, J. K. et al., "Clinical and Radiographic Outcomes of Anterior Lumbar Interbody Fusion Using Recombinant Human Bone Morphogenetic Protein-2", Spine vol. 27, No. 21, 2002, 2396-2408.
Burt, David W., "Evolutionary Grouping of the Transforming Growth Factor-Beta Superfamily", Biochem. Biophys. Res. Commun. vol. 184 Issue 2, 1992, 590-595.
Busch, Stephen J. et al., "Trans-Repressor Activity of Nuclear Glycosaminoglycans on Fos and Jun/AP-1 Oncoprotein-Mediated Transcription", J. Cell. Biol. vol. 116, 1992, 31-42.
Carmeliet, Peter et al., "Growing Better Blood Vessels", Nature Biotechnology vol. 19, 2001, 1019-1020.
collagraft.rtm. Product Description, Zimmer, Inc. (2003).

Courty, Jose et al., "Mitogenic Properties of a New Endothelial Cell Growth Factor Related to Pleiotrophin", Biochem. Biophys. Res. Commun. vol. 180 Issue 1, 1991, 145-151.
Dawson, Philip E. et al., "Synthesis of Native Proteins by Chemical Ligation", Annu. Rev. Biochem, 2000, 69, 2000, 923-960.
Dikov, Michael M. et al., "A Functional Fibroblast Growth Factor-1 Immunoglobulin Fusion Protein", The Journal of Biological Chemistry vol. 273, No. 25, 1998, 15811-15817.
Doerks, Tobias, "Protein annotation: detective work for function prediction", Trends in Genetics vol. 14 No. 6, Jun. 1998, 248-250.
Dubrulle, Julien et al., "FGF Signaling Controls Somite Boundary Position and Regulates Segmentation Clock Control of Spatiotemporal Hox Gene Activation", Cell vol. 106 Issue 2, 2001, 219-232.
Engstrom, Ulla et al., "Identification of a Peptide Antagonist for Platelet-Derived Growth Factor", The Journal of Biological Chemistry, (1992) vol. 267, 16581-16587.
Eom, Khee D. et al., "Tandem Ligation of Multipartite Peptides with Cell-Permeable Activity", J. Am. Chem. Soc., 2003,125, 2003, 73-83.
Feeley, Brian et al., "Influence of BMP's on the Formation of Osteoblastic Lesions in Metastatic Prostate Cancer", Journal of Bone and Mineral Research, vol. 20 No. 12, 2005, 2189-2199.
Fekete, Donna, "Ear rings: FGF3 involvement comes full circle", Trends in Neurosci., vol. 23 No. 8, 2000, 332.
Fenstermaker, Robert A. et al., "A Cationic Region of the Platelet-Derived Growth Factor (PDGF) A-Chain (Arg159-Lys160-Lys161) is Required for Receptor Binding and Mitogenic Activity of the PDGF-AA Homodimer", J. Biol. Chem., vol. 268 No. 14, 1993, 10482-10489.
Fox, John E., "Multiple Peptide Synthesis", Mol. Biotechnol., vol. 3 No. 3, 1995, 249-258.
Gay, Cyril G. et al., "Interleukin 1 regulated heparin-binding growth factor 2 gene expression in vascular smooth muscle cells", Proc. Natl. Acad. Sci. USA, vol. 88, Jan. 1991, 296-300.
Gemel, Joanna, "Structure and Sequence of Human FGF8", Genomics vol. 35 Issue 1, 1996, 253-257.
Gilboa, Lilach et al., "Bone Morphogenetic Protein Receptor Complexes on the Surface of Live Cells: A New Oligomerization Mode for Serine/Threonine Kinase Receptors", Md. Biol. Cell vol. 11 No. 3, 2000, 1023-1035.
Greene, J. M. et al., "Identification and Characterization of a Novel Member of the Fibroblast Growth Factor Family", Eur J. Neurosci vol. 10, No. 5, 1998, 1911-1925.
Hampton, Brian S. et al., "Structural and Functional Characterization of full-length Heparin-Binding Growth Associated Molecule", Mol. Biol. Cell. vol. 3 Issue 1, 1992, 85-93.
Hanada, Keigo et al."Stimulatory Effects of Basic Fibroblast Growth Factor and Bone Morphogenetic Protein-2 on Osteogenic Differentiation of Rat Bone Marrow-Derived Mesenchymal Stem Cells", J. Bone Miner Res. vol. 12 No. 10, 1997, 1606-1614.
Hasan, Maemunah et al., "IL-12 is a Heparin-Binding Cytokine", The Journal of Immunology vol. 162, 1999, 1064-1070.
Healy, Kevin et al., "Designing biomaterials to direct biological responses", Ann N Y Acad Sci. 875, 1999, 24-35.
Higashiyama, Shigeki et al., "A Heparin-Binding Growth Factor Secreted by Macrophage Like Cells that is Related to EGF", Science vol. 251 No. 4996, 1991, 936-939.
Hoke, David E. et al., "A Heparin Binding Synthetic Peptide from Human HIP/RPL29 Fails to Specifically Differentiate Between Anticoagulantly Active and Inactive Species of Heparin", Journal of Negative Results in BioMedicine vol. 2. No. 1, 2003,1-10.
Hoodless, Pamela A et al., "MAORI, a MAD-Related Protein That Functions in BMP2 Signaling Pathways", Cell vol. 85 No. 4, 1996, 489500.
Hoshikawa, Masamitsu et al., "Structure and Expression of a Novel Fibroblast Growth Factor, FGF-17, Preferentially Expressed in the Embryonic Brain", Biochem. Biophys. Res. Commun. vol. 244 No. 1, 1998, 187-191.
Hsu, David R et al., "The Xenopus Dorsalizing Factor Gremlin Identifies a Novel Family of Secreted Proteins that Antagonize BMP Activities", Mol, Cell vol. 1 No. 5, 1998, 673-683.

(56) References Cited

OTHER PUBLICATIONS

Hsu, Hailing et al., "Tumor Necrosis Factor Receptor Family Member RANK Mediates Osteoclast Differentiation and Activation Induced by Osteoprotegerin Ligand", Proc. Natl. Acad. Sci. (1999) vol. 96, 35403545.

Hu, Mickey C et al., "FGF-18, a Novel Member of the Fibroblast Growth Factor Family, Stimulates Hepatic and Intestinal Proliferation", Mal. Cell Biol. vol. 18 No. 10, 1998, 6063-6074.

Huber, Daniel et al., "Amino-Terminal Sequences of a Novel Heparin-Binding Protein with Mitogenic Activity for Endothelial Cells from Human Bovine, Rat, and Chick Brain: High Interspecies Homology", Neurochem. Res. vol. 15, 1990, 435-439.

Iida, Shinya et al., "Human hst-2 (FGF-6) Oncogene: cDNA Cloning and Characterization", Oncogene vol. 7 No. 2, 1992, 303-309.

Iwasaki, Shoji et al., "Specific Activation of the p38 Mitogen-activated Protein Kinase Signaling Pathway and Induction of Neurite Outgrowth in PC12 Cells by Bone Morphogenetic Protein-2", J. Biol. Chem. vol. 274 No. 37, 1999, 26503-26510.

Jeffers, Michael et al., "Identification of a Novel Human Fibroblast Growth Factor and Characterization of its Role in Oncogenesis", Cancer Res. vol. 61, No. 7, 2001, 3131-3138.

Katsuura, Mieko et al., "The NH2-terminal region of the active domain of sonic hedgehog is necessary for its signal transduction", FEBS Lett. vol. 447 No. 2-3, 1999.

Kawabata, Masahiro, "Cloning of a Novel Type II Serine/Threonine Kinase Receptor through Interaction with the Type I Transforming Growth Factor-13 Receptor", J. Biol. Chem. vol. 270 No. 10, 1995, 5625-5630.

Kinto, Naoki et al., "Fibroblasts expressing Sonic hedgehog induce osteoblast differentiation and ectopic bone formation", FEBS Lett. vol. 404 No. 2-3, 1997, 319-323.

Kirsch, Thomas et al., "BMP-2 Antagonists Emerge from Alterations in the Low-Affinity Binding Epitope for Receptor BMPR-II", EMBO Journal, vol. 19, No. 13, 2000, 3314-3324.

Kleeman, Thomas J. et al., "Laparoscopic Anterior Lumbar Interbody Fusion with rhBMP-2: A Prospective Study of Clinical and Radiographic Outcomes", Spine vol. 26, No. 24, 2001, 2751-2756.

Kloen, P et al., "BMP signaling components are expressed in human fracture callus", Bone 33, 2003, 362-371.

Kochendoefer, Gerd et al., "Design and Chemical Synthesis of Homogenous Polymer-Modified Erythropotesis Protein", Science, vol. 299, Feb. 7, 2003, 884-887.

Kok, L. D. S. et al., "Cloning and Characterization of a cDNA Encoding a Novel Fibroblast Growth Factor Preferentially Expressed in Human Heart", Biochem. Biophys. Res. Comm. vol. 255 No. 3, 1999, 717-721.

Konishi, Sadahiko et al,, "Hydroxyapatite Granule Graft Combined with Recombinant Human bone Morphogenic Protein-2 for Solid Lumbar Fusion", Journal of Spinal Disorders & Techniques, vol. 15, No. 3, 2002, 237-244.

Kuo, Ming-Der, "Characterization of Heparin-Binding Growth-Associated Factor Receptor in NIH 3T3 Cells", Biochem. Biophys. Res. Commun. vol. 182 Issue 1, 1992, 188-194.

Lanford, R., "Effect of Basic and Nonbasic Amino Acid Substitutions on Transport Induced by Simian Virus 40 T-Antigen Synthetic Peptide Nuclear Transport Signals." Mol. Cell. Biol. (1988) 8(7):2722-2729.

Laredo, James et al., "Silyl-heparin bonding improves the patency and in vivo thromboresistance of carbon-coated polytetrafluoroethylene vascular grafts", The Midwestern Vascular Surgical Society, vol. 39, No. 5, 2004, 1059-1065.

LeGeros et al., J. Mater. Sci. Mater. Med., 2003, vol. 14(3):201-209.

Lin, Xinhua, "Multidomain Synthetic Peptide B2A2 Synergistically Enhances BMP-2 In Vitro", Journal of Bone and Mineral Research vol. 20, No. 4, 2005, 693-703.

Lin, Xinhua et al., "A Synthetic, Bioactive PDGF Mimetic with Binding to Both a-PDGF and p-PDGF Receptors", Growth Factors vol. 25 No. 2, 2007, 87-93.

Lin, Xinhua et al., "Augmentation of Demineralized Bone Matrix by a Synthetic FGF-2 Mimetic", Journal of Bone and Mineral Research vol. 20, No. 9, Suppl. 1, 2005, S344-S345.

Lin, Xinhua et al., "Augmentation of Osseous Phenotypes In Vivo with a Synthetic Peptide", Journal of Orthopaedic Research, 2007, 531-539.

Lin, Xinhua et al., "Synthetic Peptide F2A4-K-NS Mimics Fibroblast Growth Factor-2 In Vitro and is Angiogenic In Vivo", International Journal of Molecular Medicine vol. 17, No. 5, 2006, 833-839.

Lu, Xinjie et al., "Preferential antagonism of the interactions of the integrin alpha IIb beta 3 with immobilized glycoprotein ligans by snake-venom RGD (Arg-Gly-Asp) proteins", Biochem J. 304, 1994, 929-936.

Marchese, C. et al., "Human Keratinocyte Growth Factor Activity on Proliferation and Differentiation of Human Keratinocytes: Differentiation Reponse Distinguishes KGF from EGF Family", J. Cellular Physiol. vol. 144 Issue 2, 1990, 326-332.

Marics, Irene et al., "Characterization of the HST-Related FGF-6 Gene, a New Member of the Fibroblast Factor Gene Family", Oncogene vol. 4 No. 3, 1989, 335-340.

Marikovsky, Moshe et al., "Appearance of Heparin-Binding EGF-like Growth Factor in Wound Fluid as a Response to Injury", Proc. Natl. Acad. Sci. (USA) vol. 90 No. 9, 1993, 3889-3893.

Massague, Joan et al., "Controlling TGF-43 signaling", Genes Dev. vol. 14 No. 6, 2000, 627-644.

McKay, Bill et al., "Summary Statement: Overview of Bone Morphogenetic Proteins for Spine Fusion", Spine vol. 27, No. 16, Suppl 1, 2002, S66-85.

McWhirter, John R. et al., "A Novel Fibroblast Growth Factor Gene Expressed in the Developing Nervous System is a Downstream Target of the Chimeric Homeodomain Oncoprotein E2A-Pbx1", Development vol. 124 No. 17, 1997, 3221-3232.

Merrifield, Bruce, "Concept and Early Development of Solid-Phase Peptide Synthesis", Methods in Enzymol, vol. 289, 1997, 3-13.

Minamide, Akihito et al., "Evaluation of Carriers of Bone Morphogenetic Protein for Spinal Fusion", Spine vol. 26, No. 8, 2001, 933-939.

Miyake, Ayumi et al., "Structure and Expression of a Novel Member, FGF-16, of the Fibroblast Growth Factor Family", Biochem. Biophys. Res. Commun. vol. 243 No. 1, 1998, 148-152.

Miyamoto, Masaaki et al., "Molecular Cloning of a Novel Cytokine cDNA Encoding the Ninth Member of the Fibroblast Growth Factor Family, Which has a Unique Secretion Pattern", Mol. Cell. Biol. vol. 13 No. 7, 1993, 4251-4259.

Miyazono, Kohei, "Positive and negative regulation of TGF-beta signaling", J. Cell Sci. vol. 113 Part 7, 2000, 1101-1109.

Morone, Michael A. et al., "The Marshall R. Urist Young Investigator Award. Gene expression during autograft lumbar spine fusion and the effect of bone morphogenetic protein 2", Clin. Orthop. vol. 351 (1998) 252-265.

Murnaghan, Mark et al., "Time for treating bone fracture using rhBMP-2: A randomised placebo controlled mouse fracture trial", Journal of Orthopaedic Research 23, 2005, 625-631.

Nakamura, Takahashi et al., "Induction of Osteogenic Differentiation by Hedgehog Proteins", Biochem. Biophys. Res. Comm. vol. 237 No. 2, 1997, 465-469.

Nakatake, Yuhki et al., "Identification of a Novel Fibroblast Growth Factor, FGF-22, Preferentially Expressed in the Inner Root Sheath of the Hair Follicle", Biochim. Biophys. Acta. vol. 1517 No. 3, 2001, 460-463.

Naruo, Ken-1CHI et al., "Novel Secretory Heparin-Binding Factors from Human Glioma Cells (Glia-Activating Factors) Involved in Glial Cell Growth", J. Biol. Chem. vol. 268 No. 4, 1993, 2857-2864.

Ngo, Thomas et al., "Computational Complexity; Protein Structure Prediction, and the Levinthal Paradox", The Protein Foling Problem and Terminary Structure Prediction, Chapter 14, 1994, 491-495.

Niikura, T. et al., "Gloval Gene Profiling in Experimental Fracture Nonunions Reveals a Down Regulation of BMP Gene Expression", 52nd Annual Meeting of the Orthopaedic Research Society, Paper No. 1673, 2006.

(56) References Cited

OTHER PUBLICATIONS

Nishimura, Tetsuya et al., "Identification of a Novel FGF, FGF-21, Preferentially Expressed in the Liver", Biochim. Biophys. Acta. vol. 1492 No. 1, 2000, 203-206.
Nohe, Anja et al., "The Mode of Bone Morphogenetic Protein (BMP) Receptor Oligomerization Determines Different BMP-2 Signaling Pathways", J. Biol. Chem. vol. 277 No. 7, 2002, 5330-5338.
Nohno, Tsutomo et al., "Identification of a Human Type II Receptor for Bone Morphogenetic Protein-4 That Forms Differential Heteromeric Complexes with Bone Morphogenetic Protein Type I Receptors", J. Biol. Chem. vol. 270 No. 38, 22522-22526, 1995.
Nyfeler, Rolf , "Peptide Synthesis via Fragment Condensation", Methods Mol. Biol., vol. 35, 1994, 303-316.
Ohbayashi, Norihiko et al., "Structure and Expression of the mRNA Encoding a Novel Fibroblast Growth Factor, FGF-18", J. Biol. Chem. vol. 273 No. 29, 1998, 18161-18164.
Ohmachi, Shigeki et al., "FGF-20, a Novel Neurotrophic Factor, Preferentially Expressed in the Substantia Nigra Pars Compacta of Rat Brain", Biochem. Biophys. Res. Commun. vol. 277 No. 2, 2000, 355-360.
Ostman, Arne et al., "Identification of Three Amino Acids in the Platelet-Derived Growth Factor (PDGF) B-chain that are Important for Binding to the PDGF B-Receptor", The Journal of Biological Chemistry, vol. 266, No. 16, Issue of Jun. 5, 1991, 10073-10077.
Paris, Francois et al., "Endothelial Apoptosis as the Primary Lesion Initiating intestinal Radiation Damage in Mice", Science vol. 293, 2001, 293-297.
Patani, G., "Bioisosterism: A Rational Approach in Drug Design." Chem. Rev. (1996) 96:3147-3176.
Pellegrini, Luca , "Role of Heparan sulfate in fibroblast growth factor signalling: a structural view", Current Opinion in Structural Biology vol. 11, No. 5, 2001, 629-634.
Poynton, Ashley R. et al., "Safety Profile for the Clinical Use of Bone Morphogenetic Proteins in the Spine", Spine vol. 27, No. 16, Suppl. 1, 2002, S40-48.
Preliminary Amendment in U.S. Appl. No. 15/230,189 (reissue of U.S. Pat. No. 8,796,212) (filed Aug. 5, 2016).
Ray, Jasohara et al., "A 10-amino acid sequence of fibroblast growth factor 2 is sufficient for its mitogenic activity on neural progenitor cells", Proc. Natl. Acad. Sci. USA vol. 94, 1997, 7047-7052.
Reddi, A. H. , "Bone Morphogenetic Proteins: From Basic Science to Clinical Applications", J. Bone Joint Surg. AM, vol. 83-8 Suppl. 1 Pt. 1, 2001, S1-S6.
Reply to Non-Final Office Action under 37 CFR .sctn. 1.111 dated Feb. 28, 2018 corresponding to U.S. Appl. No. 15/230,189.
Richardson, Thomas P. et al., "Polymeric system for dual growth factor delivery", Nature Biotechnology vol. 19, 2001, 293-297.
Rosenzweig, Bradley et al., "Cloning and characterization of a human type II receptor for bone morphogenetic proteins", Proc. Natl. Acad. Sci. USA, vol. 92 No. 17, 1995, 7632-7636.
Rusnati, Marco et al., "avB3 Integrin Mediates the Cell-adhesive Capacity and Biological Activity of Basic Fibroblast Growth Factor (FGF-2) in Cultured Endothelial Cells", Molecular Biology of the Cell vol. 8, 1997, 2449-2461.
Saito, Atsuhiro et al., "Activation of osteo-progenitor cells by a novel synthetic peptide derived from the bone morphogenetic protein-2 knuckle epitope", Biochimica et Biophysica Acta 1651, 2003, 60-67.
Saito, Atsuhiro et al., "Prolonged ectopic calcification induced by BMP-2-derived synthetic peptide", Journal of Biomedical Materials Research Part A, vol. 70 No. 1, 2004, 115-121.
Sakamoto, Hiromi et al., "Adenovirus-mediated transfer of the HST-1 (FGF4) gene induces increased levels of platelet count in vivo", Proc. Natl. Acad. Sci. USA, vol. 91 No. 26, 1994, 12368-12372.
Seol, Yang-Jo et al., "Enhanced osteogenic promotion around dental implants with synthetic binding motif mimicking bone morphogenetic protein (BMP)-2", Journal of Biomedical Materials Research Part A, vol. 77 No. 3, 2006, 599-607.

Shen, Wei-Chiang et al., "Poly(l-lysine) has different membrane transport and drug-carrier properties when complexed with heparin", Proc Nati Acad Sci USA vol. 78, No. 12, Dec. 1981, 7589-93.
Shimada, Takahashi et al., "Cloning and Characterization of FGF23 as a Causative Factor of Tumor-induced Osteomalacia", Proc. Natl. Acad. Sci. (USA) vol. 98 No. 11, 2001, 6500-6505.
Sidhu, Sachdev , "Phage Display for Selection of Novel Binding Peptides", Methods Enzymol, vol. 328, 2000, 333-363.
Skolnick, Jeffrey et al., "From genes to protein structure and function: novel applications of computational approaches in the genomic era", TIBTECH vol. 18, Jan. 2000, 34-39.
Smith, Temple F. et al., "The challenges of genome sequence annotation of "The devil is in the details"", Nature Biotechnology, vol. 15, Nov. 1997, 1222-1223.
Sood, R. et al., "MDS1/EVI1 enhances TGF-B1 signaling and strengthens its growth-inhibitory effect, but the leukemia-associated fusion protein AML1/MDS1/EVI1, product of the t(3:21), Abrogates growth-inhibition in response to TGF-B1", Leukemia vol. 13, 1999, 348357.
Spinella-Jaegle, Sylviane et al., "Sonic hedgehog increases the commitment of pluripotent mesenchymal cells into the osteoblastic lineage and abolishes adipocytic differentiation", J. Cell Sci. vol. 114 Part 11, 2001, 2085-209.
Suzuki, Yoshihisa et al., "Alginate hydrogel linked with synthetic oligopeptide derived from BMP-2 allows ectopic osteoinduction in vivo", J. Biomed. Mater. Res. vol. 50 No. 3, 2000, 405-409.
Takizawa, Takuma et al., "Directly Linked Soluble 1L-6 Receptor-IL-6 Fusion Protein Induces Astrocyte Differentiation from Neuroepithelial Cells Via Activation of STAT3", Cytokine vol. 13, 2001, 272-279.
Tanaka, H. et al., "Involvement of bone morphogenic protein-2 (BMP-2) in the pathological ossification process of the spinal ligament", Rheumatology vol. 40 (2001) 1163-1168.
Tanaka, Shinji et al., "A Novel Isoform of Human Fibroblast Growth Factor 8 is Induced by Androgens and Associated with Progression of Esophageal Carcinoma", Dig. Dis. Sci. vol. 46 No. 5, 2001, 1016-1021.
Tong, Yen et al., "Peptide surface modification of poly(tetrafluoroethylene-co-hexafluoropropylene) enhances its interaction with central nervous system nuerons", J Biomed Mater Res 42, 1998, 85-95.
Tung, Ching-Hsuan et al., "Novel branching membrane translocational peptide as gene delivery vector", Bioorg Med Chem 10(11), 2002, 3609-3614.
Varkey, Mathew et al., "Growth factor delivery for bone tissue repair: an update", Expert Opin. Drug Deliver. vol. 1, No. 1, 2004, 19-34.
Verrecchio, Angela , "Design of Peptides with High Affinities for Heparin and Endothelial Cell Proteoglycans", The Journal of Biological Chemistry, vol. 275, No. 11, Mar. 17, 2000, 7701-7707.
Wade, John D. et al., "Solid Phase Peptide Synthesis; Recent Advances and Applications", Austral. Biotechnol., vol. 3 No. 6, 1993, 332-336.
Wang, Jian-Sheng , "Basic fibroblast growth factor and bone inductionin rats", Acta. Orthop. Scand. vol. 64 No. 5, 1993, 557-561.
Wells, James A. , "Additivity of Mutational Effects in Proteins", American Chemical Society, vol. 29, No. 37, Sep. 18, 1990, 85098516.
White, Kyle K. et al., "Mineralization of substrates modified with BMP-7 derived peptides", American Society of Mechanical Engineers BED—vol. 50, 2001, 201-202.
Wozney, John M. , "Overview of Bone Morphogenetic Proteins", Spine vol. 27, No. 16, Suppl 1, 2002, S2-S8.
Xie, Ming-Hong et al., "FGF-19, a Novel Fibroblast Growth Factor with Unique Specificity for FGFR4", Cytokine vol. 11 No. 10, 1999, 729-735.
Xu, Jingsong et al., "Genomic Structure, Mapping, Activity and Expression of Fibroblast Growth Factor 17", Mechanisms of Development vol. 83, 1999, 165-178.

(56) References Cited

OTHER PUBLICATIONS

Yamashita, Tetsuo et al., "Identification of a Novel Fibroblast Growth Factor, FGF-23, Prefrentially Expressed in the Ventrolateral Thalamic Nucleus of the Brain", Biochem. Biophys. Res. Commun. vol. 277 No. 2, 2000, 494-498.

Yano, Akira et al., "RGD motif enhances immunogenicity and adjuvanicity of peptide antigens following intranasal immunization", Vaccine 22(2), 2003, 237-243.

Yoneda, Atsuko, "Engineering of an FGF-proteogiycan fusion protein with heparin-independent, mitogenic activity", Nature Biotechnology vol. 18, Jun. 2000, 641-644.

Yuasa, Takahito, "Sonic hedgehog is involved in osteoblast differentiation by cooperating with BMP-2", J. Cell Physiol. vol. 193 No. 2, 2002, 225-232.

Zamora, Paul O. et al., "Local Delivery of Basic Fibroblast Growth Factor (bFGF) Using Adsorbed Silyl-heparin, Benzyl-bis(dimethylsilylmethyl)oxycarbamoyl-heparin", Bioconjugate Chem. vol. 13, No. 5, 2002, 920-926.

Zhan, Xi et al., "The Human FGF-5 Oncogene Encodes a Novel Protein Related to Fibroblast Growth Factors", Mol. Cell Biol. vol. 8 No. 8, 1988, 3487-3495.

Zimmerman, Lyle B. et al., "The Spemann Organizer Signal noggin Binds and Inactivates Bone Morphogenetic Protein 4", Cell vol. 86 No. 4, 1996, 599-606.

\* cited by examiner

COMPOSITION AND METHOD FOR DELIVERY OF BMP-2 AMPLIFIER/CO-ACTIVATOR FOR ENHANCEMENT OF OSTEOGENESIS

CROSS REFERENCE TO RELATED APPLICATIONS

This application is a continuation of U.S. patent application Ser. No. 16/358,343 filed Mar. 19, 2019 (now U.S. Pat. No. 11,078,244), which was filed as a divisional of U.S. patent application Ser. No. 14/452,304 filed Aug. 5, 2014 (now U.S. Pat. No. 10,246,499), which is a continuation of U.S. patent application Ser. No. 13/186,165 filed Jul. 19, 2011 (now U.S. Pat. No. 8,796,212), which is a divisional of U.S. patent application Ser. No. 11/767,391 filed Jun. 22, 2007 (now U.S. Pat. No. 7,981,862), which claims priority to and the benefit of U.S. Provisional Patent Application Ser. No. 60/805,594 filed Jun. 22, 2006, the specification of each of which is incorporated herein by reference.

BACKGROUND

The present invention relates to compositions that result in enhanced osteogenesis across a broad range of bony repair indications and methods of using the compositions in a delivery vehicle for improved repair of bony lesions.

The U.S. published application 2005/0196425 to Zamora et al. entitled. "Positive modulator of BMP-2" teaches a compound comprising a bone morphogenic protein-2 (BMP-2) analogue which is useful to repair bone lesions and a method in which the compound can augment endogenous or exogenously added BMP-2 activity. It further teaches that there are a number of commercially available bone graft substitutes that are osteoconductive that the BMP-2 modulator compounds could modify. The osteoconductive materials included a number of calcium phosphate containing composites. The compound is an additive to bone matrix or bone graft materials or controlled or associated with drug delivery devices among others. US 2005/0196425, however, does not disclose peptide and osteoconductive formulations that permit efficient peptide binding to osteoconductive materials, controlled differential release through manipulating the osteoconductive composition, manipulating the peptide composition, concentration of the compound attached thereto, and/or manipulating the calcium sulfate concentration. For this application, the positive modulator of BMP-2 will be referred to as the co-activator/amplifier.

Osteoconduction can be described as the process of forming bone on a graft material that is placed into a void in a bony environment. Broadly speaking osteoconduction means that bone grows on a surface. Osteoconduction requires a scaffold for cells to move into the graft site and produce bone. Scaffold materials can be categorized into four types: allograft bone, natural polymers (hyaluronates, fibrin, carboxymethyl cellulose, chitosan, collagen, etc.), synthetic polymers (polylactic acid (PLA), polyglycolic acid (PGA)), and inorganic materials (e.g. hydroxyapatite (HA), tricalcium phosphate (TCP), calcium sulfate (CaS)). A number of synthetic osteoconductive bone graft materials have been developed for purposes of filling boney voids. These graft materials, however, are only osteoconductive and provide a scaffold for viable bone healing, including ingrowth of neovasculature and the infiltration of osteogenic precursor cells into the graft site.

Osteoinduction is the process by which osteogenesis is induced and is a process regularly seen in any type of bone healing. Osteoinduction implies the recruitment of immature cells and the stimulation of these cells to develop into preosteoblasts. In a bone healing environment, the majority of bone healing is dependent on osteoinduction. This process is typically associated with the presence of bone growth factors (principally bone morphogenic proteins) within the bone healing environment.

Osteoinduction can be influenced by a number of proteins or growth factors, growth or new blood vessels (angiogenesis). These proteins cause healing bone to vascularize, mineralize, and function mechanically. They can induce mesenchymal-derived cells to differentiate into bone cells. The proteins that enhance bone healing include the bone morphogenetic proteins, insulin-like growth factors, transforming growth factors, platelet derived growth factor, and fibroblast growth factor among others. The most well-known of these proteins are the BMPs which induce mesenchymal cells to differentiate into bone cells. Other proteins influence bone healing in different ways. Transforming growth factor and fibroblast growth factor regulate angiogenesis and can influence bone formation and extracellular matrix synthesis. Extracellular matrix molecules such as osteonectin, fibronectin, osteonectin, laminin, and osteocalcin promote cell activation, cell attachment and facilitate cell migration.

While any healing bone lesion is an osteoinductive environment, not all osteoinductive environments (bone lesions) have the ability to undergo a full or complete healing. This has led to the use of recombinant bone morphogenic proteins to induce osteoinduction in graft materials thereby to induce stem cells to differentiate into mature bone cells.

U.S. Pat. No. 7,041,641 to Rueger et al. demonstrates any number of bone morphogenic proteins (BMPs) and growth factors combined with a number of scaffolds (including HA and TCP) and a binder for bone repair. These graft materials are, however, expensive and can lead to exuberant or ectopic bone production.

U.S. Pat. No. 6,949,251 Dalal et al. discloses a beta Tricalcium Phosphate (BTCP) particle with any number of BMPs and/or a binder (CMC, Hyaluronate, etc.) for bone repair.

U.S. Pat. No. 6,426,332 Rueger et al. discloses OTCP as an osteoconductive material with any number of bioactive agents combined therewith, for example BMP-2. The bioactive agent is dispersed in a biocompatible, non-rigid amorphous carrier having no defined surfaces, wherein said carrier is selected from the group consisting of poloxamers; gelatins; polyethylene glycols (PEG); dextrans; and vegetable oils.

A commercially available product for periodontal bone repair, GEM-21S™, utilizes a β-TCP granule coated with platelet derived growth factor "PDGF." Saito et al. (JBMR 77A: 700-6 (2006)) utilized the 73-92 peptide derived from 73-92 of the BMP-2 knuckle epitope. This peptide was coated on aTCP (OCTCP) cylinders and implanted in 20 mm long defects. Konishi et al. (J. Spine Disorders & Tech.) and Minamide et al. (Spine 2001 26 (8): 933-9) demonstrated BMP combined with hydroxyapatite granules for lumbar fusion.

Delivery of small molecules (such as peptides) for therapeutic indications is usually accomplished by various encapsulation technologies-microspheres, for example, in which the molecule is encapsulated in a vesicle which degrades over time to release the peptide. Delivery of a small molecule from the surface of a medical device has been challenging as small molecules rarely have physical properties that provide sufficient binding properties to a biomaterial surface. Often, the peptide is covalently attached to the surface in an effort to prevent rapid release (Saito et al., J. Biomed Mater Res 70A: 115-121 (2004; Seol Y-J et al., J. Biomed. Mater Res (A) (2006)) (Varkey et al., Expert Opin. Drug Deliv. 2004 Nov.; 1 (1): 19-36. Growth factor delivery for bone repair, Varkey et al.). One drawback of covalent crosslinks is the molecule is unable to release and influence the surrounding osteoconductive environment.

The delivery kinetics and quantities of a synthetic compound comprising a BMP-2 amplifier/co-activator may be specifically tailored to the indication of choice. It should be recognized that after a bony lesion is made, there is a reparative response that results in the cellular production of BMP-2, and furthermore, that this production occurs over a given time sequence with an upregulation period eventually followed by downregulation. Niikura et al. (2006 ORS, #1673) measured BMP-2 production over time in standard fractures and non-unions in rats and demonstrated less BMP-2 production in non-unions than in standard fractures and increasing amounts of BMP-2 up to 21 days followed by a decline in expression at 28 days. BMP-2 expression has been detected in the human fracture callus (Kloen et al., 2003, 362-371). Furthermore, Murnaghan et al. (JOR 2005, 23:625-631) demonstrated in a mouse fracture trial that BMP-2 administered to the fracture at day 0 or 4 produced greater repair than that introduced at day 8. It should be noted that in this case BMP-2 is timed with the production of stem cells that can be differentiated to bone and is not timed with endogenous BMP-2 production.

A synthetic growth factor identified as B2A2-K-NS was first disclosed by Zamora et al. in U.S. patent application titled Positive Modulator of Bone Morphogenic Protein-2 having Ser. No. 11/064,039 filed Feb. 22, 2005 in addition to disclosing various other peptides. However, it was not disclosed to combine the synthetic growth factor with an osteoconductive material as a composition for treating bone lesions.

There is, therefore, a need for a composition which can act as a bone void filler material and which is comprised of a synthetic growth factor analogue which can act as an amplifier/co-activator of osteoinduction, and which can attached to and released from an osteoconductive material to enhance boney repair and healing processes.

There are also number of surgical procedures in orthopedics wherein augmentation of bone repair would be particularly beneficial including fusion procedures including those of the spine and ankle; in filling the voids in bones resultant from traumatic injury; in the treatment of non-unions; fracture healing in all skeletal elements; in fixation of internal hardware such as rods, plates, screws, and the like; in concert with spinal cages or vertebral body replacements; and in the augmentation of implanted wedges, pedicle screws, or rings. These types of procedures and the associated hardware would be known to those skilled in the art.

SUMMARY OF THE INVENTION

According to one aspect, the present invention describes compositions that result in enhanced osteogenesis across a broad range of bony repair indications and wherein a synthetic growth factor analogue attached to and released from an osteoconductive material acts as an amplifier/co-activator of osteoinduction and results in enhanced boney repair and healing processes. Alternatively, the synthetic growth factor analogue is affixed to the osteoconductive material and is not released.

According to another aspect, the present invention provides a delivery vehicle containing the following components: an osteoconductive scaffold and a synthetic growth factor analogue acting as an amplifier/co-activator of osteoinduction; wherein the scaffold is capable of binding and releasing the synthetic growth factor, and preferably at a rate that coincides with the presence of endogenous BMP-2.

In another aspect of the invention the correct release parameters of the synthetic growth factor analogue is related to the type of bone lesion and results in enhanced osteogenesis. The delivery kinetics and quantities of a synthetic growth factor analogue may be specifically tailored to the indication of choice. For example if the synthetic growth factor analogue is intended to augment the activity of endogenous BMP-2, delivery characteristics in a fracture repair should require a more rapid delivery as compared to a spine fusion in which a much slower delivery over a much longer period would likely be preferred.

In that regard, it should be recognized that after a bony lesion is made, there is a reparative response that results in the cellular production of BMP-2, and, furthermore, that this production occurs over a given time. Furthermore, it should be recognized that the quantity of endogenous BMP-2 produced is dependent upon many factors including the surface area of injured bony tissue, the number of viable osteoblast cells, the rate of repair, etc. Non-critical size defects have sufficient reparative cells and BMP-2 to repair the defect without an exogenous biomaterial. Furthermore, small, segmental fractures may produce a much greater amount of host BMP-2 relative to the defect volume than larger defects that have less bony surface area.

According to yet another aspect, the present invention provides a composition comprising a synthetic growth factor peptide analogue comprising a non-growth factor heparin binding region, a liker and a sequence that binds specifically to a cell surface receptor; and an osteoconductive material comprising one or more of an inorganic material, a synthetic polymer, a natural polymer, an allograft bone, or combination thereof, wherein the synthetic growth factor analogue is attached to and can be released from the osteoconductive material and is an amplifier/co-activator of osteoinduction.

A composition comprising a synthetic growth factor analogue of Formula II:

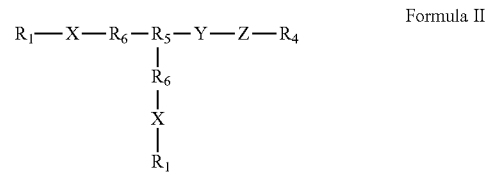

Formula II wherein:
X is a peptide chain that (i) has a minimum of three amino acid residues, (ii) has a maximum of about fifty amino acid residues, and (iii) binds specifically to a cell surface receptor;
$R_1$ is independently hydrogen, such that the terminal group is $NH_2$, an acyl group with a linear or branched $C_1$ to $C_{17}$ alkyl, aryl, heteroaryl, alkene, alkenyl, or aralkyl chain including an N-terminus $NH_2$, $NH_3^+$, or NH group or a corresponding acylated derivative, or is amino acid, a dipeptide, or a tripeptide with an N-terminus $NH_2$, $NH_3^+$, or NH group;

$R_6$ is independently a linker comprising a chain from 0 to about 15 backbone atoms covalently bonded to $R_5$ when the linker is greater than 0 atoms;

$R_5$ is a trifunctional alpha amino acid residue, wherein X is covalently bonded through a side chain of $R_6$;

$R_4$ is OH such that the terminal group is a carboxyl, $NH_2$, an acyl group with a linear or branched $C_1$ to $C_{17}$ alkyl, aryl, heteroaryl, alkene, alkenyl, or aralkyl chain including an N-terminus $NH_2$, $NH_3^+$, or NH group or a corresponding acylated derivative, or $NH-R_1$;

Y is a linker comprising a chain from 0 to about 50 backbone atoms covalently bonded to $R_5$ and Z; and Z is a non-signaling peptide chain that includes a heparin binding domain comprising an amino acid sequence that comprises (i) a minimum of one heparin binding motif, (ii) a maximum of about ten heparin binding motifs, and (iii) a maximum of about thirty amino acids; and an osteoconductive material comprising one or more of an inorganic material, synthetic polymer, natural polymers, allograft bone, or combination thereof. In a preferred embodiment, the synthetic growth factor analogue is attached to and can be released from the osteoconductive material and is an amplifier/co-activator of osteoinduction.

In another aspect of the invention, the synthetic growth factor analogue that is attached to and released from an osteoconductive material is the peptide B2A2-K-NS. B2A2-K-NS acts as an amplifier/co-activator of BMP-2 and via that processes amplifies osteoinduction and results in enhanced boney repair and healing processes. B2A2-K-NS is of the following sequence: AISMLYLDENEKVVLKK (AISMLYLDENEKVVLK) HxHxHxRKRLDRIARNH2.

B2A2-K-NS binds to inorganic granules including 100% hydroxyapatite (HA) and biphasic compositions of HA, for example, 20:80 (HA: TCP) and 60:40 (HA: TCP) but not limited thereto. B2A2-K-NS also binds to organic material (for example, collagen sponge). B2A2-K-NS is released at different rates from several inorganic granules. The magnitude of peptide release is altered by peptide concentration and/or by the peptide amino acid composition. For example, widely distributed positive charges on the peptide results in less release (e.g. more tightly bound peptide) than peptide that lacked broad positive charge distribution. Importantly, a rabbit spine fusion study demonstrated that B2A2-K-NS bound to and released from a 20:80 (HA: TCP) granule and resulted in optimal release characteristics that enhanced endogenous BMP-2 activity, which resulted in enhanced bone formation and spine fusion.

In another aspect of the invention the synthetic growth factor analogue that is attached to and released from an osteoconductive material co-activators or amplifies or modifies a biological process such as blood vessel formation, inflammation, cell growth, cell binding to osteoconductive scaffold or chemotaxis that is related to bone formation. Similarly, others of Formulas I and II which include embodiments wherein the X region is all or a portion, or a homolog of all or a portion of SEQ ID NOs 7-19 but not limited thereto.

Additionally, the following synthetic growth factor analogues may so be used: B7A with the sequence as follows: VLYFDDSSNVILKKK (VLYFDDSSNVILKK) HxHxHxRKRKLERIAR-amide wherein Hx is aminohexanoic acid. B7A enhances BMP-2 activity by increasing activity of BMP-7 and BMP-2.

LA-2 which stimulates cell adhesion and migration may also be used and has the sequence as follows: SIKVAVAAK (H-SIKVAVAA) HxHxHxRKRKLERIAR-amide.

Increasing the number of cells that bind to an osteoconductive scaffold would indirectly enhance the activity of endogenous BMP-2.

Also, F2A4-K-NS which induces blood vessel growth can be used to enhance bone formation. F2A is a peptide mimetic of basic FGF, and is also referred to as F2A. Both that peptide and bFGF have been previously demonstrated to enhance angiogenesis. Increasing angiogenesis has been previously demonstrated to enhance bone formation and thus would be expected to increase the bone formation activity of BMP-2 in concert. F2A4-K-NS has the sequence: YRSRKYSSWYVALKRK (H-YRSRKYSSWYVALKR) HxHxHxRKRLDRIAR-amide.

Similarly, the synthetic growth factor analogue VA5, which is a mimetic of vascular endothelial growth factor may so be used and has the following sequence:

WFLLTMAAK (WFLLTMAA) HxHxHxRKRKLERIAR-amide.

Also, the synthetic growth factor analogue SD-2, which mimics aspects of stromal derived growth factor-1, may be used to increase chemotaxis and localization of circulating progenitor cells to the bone lesion site. SD-2 has the sequence: KWIQEYLEKK (KWIQEYLEK) HxHxHxRKRKLERIAR-amide.

This invention can also utilize other heparin binding growth factor analogues based on vascular endothelial growth factor which increase cell growth and be related to platelet derived growth factor or transforming growth factor-beta and the like which would act in accord with this invention to enhance osteoinduction and accelerate bone repair.

Similarly, synthetic growth factor analogues which bind directly to the BMP-2 or its receptor generally similar to B2A2-K-NS described herein, can also be used to amplify biological processes that increase bone formation. Release of these peptides would occur over the correct time so as to optimize this related biological process.

In another aspect of the invention the composition of this invention may be used with exogenously supplied osteoinductive agents. These osteoinductive agents can include demineralized bone matrix other form of allograft material.

In another aspect of the invention the composition of this invention may be used with exogenously supplied osteoinductive agents based on recombinant technologies. These recombinant osteoinductive agents include BMP-2, BMP-7 (OP-1), GDF-5 (MP-52), TGF-beta1 and others that are known to those skilled in the art.

In another aspect of the invention the composition of this invention may be used with autograft bone or bone marrow aspirate that is added with the bone replacement graft at the lesion site.

Additional objects and advantages of the present invention will be apparent in the following detailed description read in conjunction with the accompanying drawing figures.

DETAILED DESCRIPTION OF THE INVENTION

Figure 1:
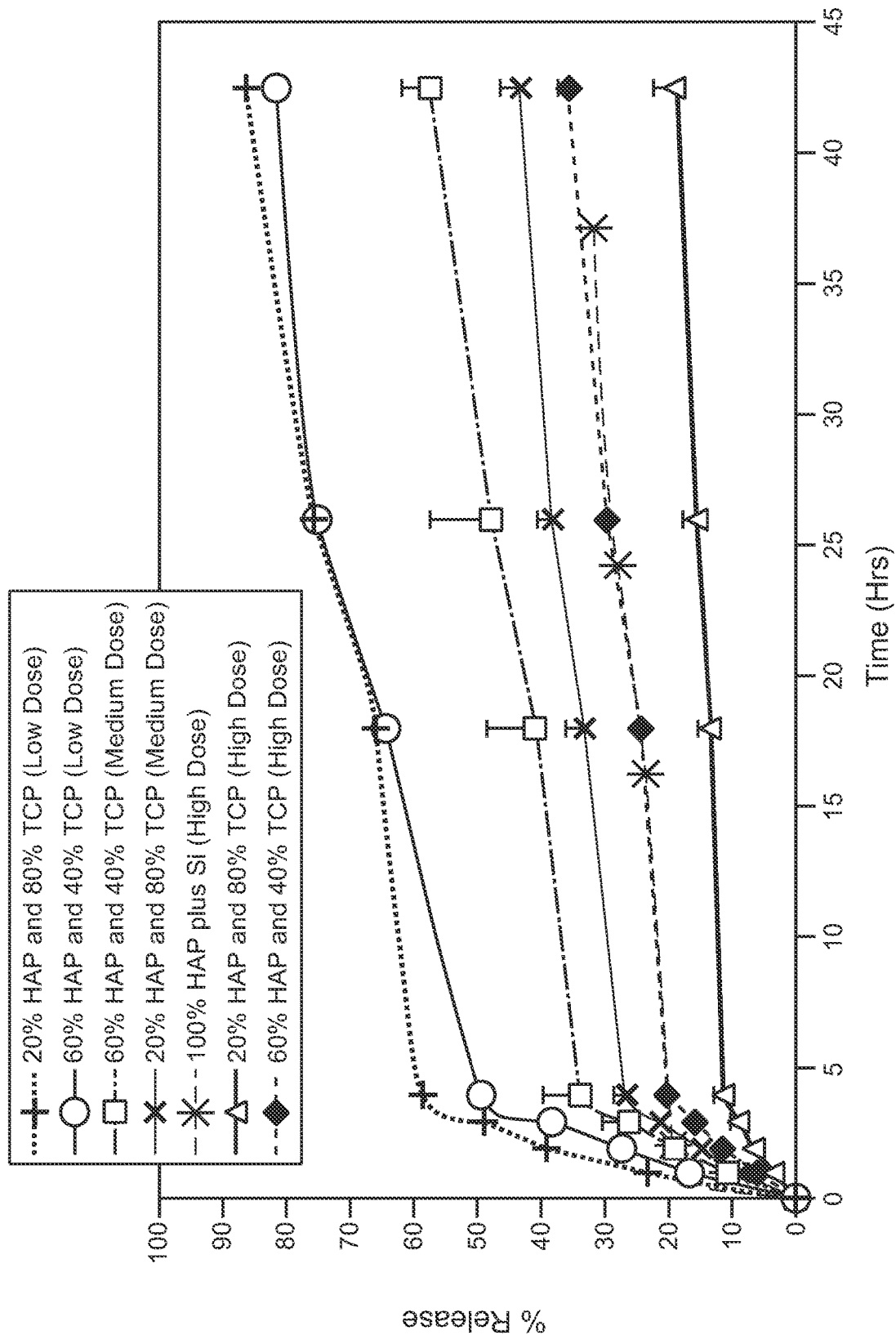
FIG. 1 illustrates a graph of B2A2-K-NS release from inorganic granules according to one embodiment of the present invention.

Definitions: As used here and elsewhere, the following terms have the meanings given.

The term "a" as used herein means one or more.

The term "alkene" includes unsaturated hydrocarbons that contain one or more double carbon-carbon bonds. Examples of such alkene groups include ethylene, propene, and the like.

The term "alkenyl" includes a linear monovalent hydrocarbon radical of two to six carbon atoms or a branched monovalent hydrocarbon radical of three to six carbon atoms containing at least one double bond; examples thereof include ethenyl, 2-propenyl, and the like.

The "alkyl" groups specified herein include those alkyl radicals of the designated length in either a straight or branched configuration. Examples of such alkyl radicals include methyl, ethyl, propyl, isopropyl, butyl, sec-butyl, tertiary butyl, pentyl, iso-pentyl, hexyl, iso-hexyl, and the like.

The term "aryl" includes a monovalent or bicyclic aromatic hydrocarbon radical of 6 to 12 ring atoms, and optionally substituted independently with one or more substituents selected from alkyl, haloalkyl, cycloalkyl, alkoxy, alkylthio, halo, nitro, acyl, cyano, amino, monosubstituted amino, disubstituted amino, hydroxy, carboxyl, or alkoxycarbonyl. Examples of an aryl group include phenyl, biphenyl, naphthyl, 1-naphthyl, and 2-naphthyl, derivatives thereof, and the like.

The term "aralkyl" includes a radical-$R^a R^b$ where $R^a$ is an alkylene (a bivalent alkyl) group and $R^b$ is an aryl group as defined above. Examples of aralkyl groups include benzyl, phenylethyl, 3-(3-chlorophenyl)-2-methylpentyl, and the like. The term "aliphatic" includes compounds with hydrocarbon chains, such as for example alkanes, alkynes, alkynes, and derivatives thereof.

The term "acyl" includes a group RCO—, where R is an organic group. An example is the acetyl group $CH_3CO$—.

A peptide or aliphatic moiety is "acylated" when an alkyl or substituted alkyl group as defined above is bonded through one or more carbonyl {—(C=O)—} groups. A peptide is most usually acylated at the N-terminus.

An "amide" includes compounds that have a trivalent nitrogen attached to a carbonyl group (—C(=O) $NH_2$).

An "amine" includes compounds that contain an amino group (—$NH_2$).

A "diamine amino acid" is an amino acid or residue containing two reactive amine groups and a reactive carboxyl group. Representative examples include 2,3-diamino propionyl amino acid, 2,4-diamino butylic amino acid, lysine, or ornithine.

The term "Hx" as used herein means aminohexanoic acid and is also sometimes abbreviated Ahx.

The term "homologous" as used herein refers to peptides that differ in amino acid sequence at one or more amino acid positions when the sequences are aligned. For example, the amino acid sequences of two homologous peptides can differ only by one amino acid residue within the aligned amino acid sequences of five to ten amino acids. Alternatively, two homologous peptides of ten to fifteen amino acids can differ by no more than two amino acid residues when aligned. In another alternative, two homologous peptides of fifteen to twenty or more amino acids can differ by up to three amino acid residues when aligned. For longer peptides, homologous peptides can differ by up to approximately 5%, 10%, 20%, 25% of the amino acid residues when the amino acid sequences of the two peptide homolog are aligned.

A "trifunctional amino acid" is an amino acid or residue with three reactive groups, one the N-terminal amine, a second the C-terminus carboxyl, and the third comprising all or a part of the side chain. Trifunctional amino acids thus include, by way of example only, diamine amino acids; amino acids with a reactive sulfhydryl group in the side chain, such as mercapto amino acids including cysteine, penicillamine, or 3-mercapto phenylalanine; amino acids with a reactive The term "synthetic growth factor analogue" as used herein may be of Formula I or II. Each synthetic growth factor analogue of the invention contains two substantially similar sequences (homodimeric sequences) at X that are analogues of a particular growth factor that binds to a growth factor receptor that may be located on the cell surface, or alternatively that bind to a growth factor receptor without being an analogue of the cognate growth factor. The homodimeric sequences may be derived from any portion of a growth factor. The synthetic GROWTH FACTOR analogue may be an analogue of a hormone, a cytokine, a lymphokine, a chemokine or an interleukin, and may bind to any growth factor receptor, for any of the foregoing.

According to one embodiment of the present invention, a composition for treatment of bone lesions comprises a synthetic growth factor analogue which acts as an amplifier/co-activator of endogenous BMP-2 and is of Formula I or II and is releasably attached to an osteoconductive material. The compound of Formula I:

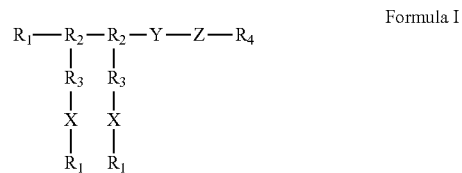

Formula I wherein:
  X is a peptide chain that (i) has a minimum of three amino acid residues, (ii) has a maximum of about fifty amino acid residues, and (iii) binds specifically to a specifically to a cell surface receptor;
  $R_1$ is independently hydrogen, such that the terminal group is $NH_2$, an acyl group with a linear or branched $C_1$ to $C_{17}$ alkyl, aryl, heteroaryl, alkene, alkenyl, or aralkyl chain including an N-terminus $NH_2$, $NH_3^+$, or NH group or a corresponding acylated derivative, or is amino acid, a dipeptide, or a tripeptide with an N-terminus $NH_2$, $NH_3^+$, or NH group;
  $R_2$ is independently a trifunctional alpha amino acid residue, wherein X is covalently bonded through a side chain of $R_2$;
  $R_3$ is independently a linker comprising a chain from 0 to about 15 backbone atoms covalently bonded to $R_2$;
  $R_4$ is OH such that the terminal group is a carboxyl, $NH_2$, an acyl group with a linear or branched $C_1$ to C$_{17}$ alkyl, aryl, heteroaryl, alkene, alkenyl, or aralkyl chain including an N-terminus NH$_2$, NH$_3^+$, or NH group or a corresponding acylated derivative, or NH—R$_1$;

Y is a linker comprising a chain from 0 to about 50 backbone atoms covalently bonded to R$_2$ and Z; and Z is a non-signaling peptide chain that includes a heparin binding domain comprising an amino acid sequence that comprises (i) a minimum of one heparin binding motif, (ii) a maximum of about ten heparin binding motifs, and (iii) a maximum of about thirty amino acids.

The compound may further comprise a linker that (i) is hydrophobic, (ii) comprises a chain of a minimum of about 9 and a maximum of about 50 backbone atoms, and (iii) is not found in Bone Morphogenic Protein-2. The compound may contain at R$_2$ an L- or D-diamine amino acid residue. In a preferred embodiment, the L- or D-diamine amino acid residue is 2,3-diamino propionyl amino acid, 2,4-diamino butylic amino acid, lysine, or ornithine.

In one embodiment, X is covalently bonded to R$_2$ and wherein the covalent bonds comprise an amide, disulfide, thioether, Schiff base, reduced Schiff base, imide, secondary amine, carbonyl, urea, hydrazone, or oxime bond. In a preferred embodiment, X is covalently bonded to R$_3$ when R$_3$>0 atoms and wherein the covalent bond comprises an amide, disulfide, thioether. Schiff base, reduced Schiff base, imide, secondary amine, carbonyl, urea, hydrazone or oxime bond. Y comprises a straight chain amino carboxylic acid.

The compound of Formula II comprising:

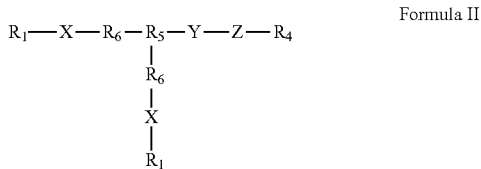

Formula II wherein:
X is a peptide chain that (i) has a minimum of three amino acid residues, (ii) has a maximum of about fifty amino acid residues, and (iii) binds specifically to a cell surface receptor;

R$_1$ is independently hydrogen, such that the terminal group is NH$_2$, an acyl group with a linear or branched C$_1$ to C$_{17}$ alkyl, aryl, heteroaryl, alkene, alkenyl, or aralkyl chain including an N-terminus NH$_2$, NH$_3^+$, or NH group or a corresponding acylated derivative, or is amino acid, a dipeptide, or a tripeptide with an N-terminus NH$_2$, NH$_3^+$, or NH group;

R$_6$ is independently a linker comprising a chain from 0 to about 15 backbone atoms covalently bonded to R$_5$, when the linker is greater than 0 atoms;

R$_5$ is a trifunctional alpha amino acid residue, wherein X is covalently bonded through a side chain of R$_6$;

R$_4$ is OH such that the terminal group is a carboxyl, NH$_2$, an acyl group with a linear or branched C$_1$ to C$_{17}$ alkyl, aryl, heteroaryl, alkene, alkenyl, or aralkyl chain including an N-terminus NH$_2$, NH$_3^+$, or NH group or a corresponding acylated derivative, or NH—R$_1$;

Y is a linker comprising a chain from 0 to about 50 backbone atoms covalently bonded to R$_5$ and Z; and Z is a non-signaling peptide chain that includes a heparin binding domain comprising an amino acid sequence that comprises (i) a minimum of one heparin binding motif, (ii) a maximum of about ten heparin binding motifs, and (iii) a maximum of about thirty amino acids.

For either of Formula I or II, the regions X and Z of the synthetic growth factor analogues include amino acid residues, and optionally the region Y includes amino acid residues. An amino acid residue is defined as —NHRCO—, where R can be hydrogen or any organic group. The amino acids can be D-amino acids or L-amino acids. Additionally, the amino acids can be α-amino acids, β-amino acids, γ-amino acids, or δ-amino acids and so on, depending on the length of the carbon chain of the amino acid.

The amino acids of the X, Y, and Z component regions of the synthetic growth factor analogues of the invention can include any of the twenty amino acids found naturally in proteins, e.g., alanine (Ala, A), arginine (Arg, R), asparagine (Asn, N), aspartic acid (Asp, D), cysteine (Cys, C), glutamic acid (Glu, E), glutamine (Gln, Q), glycine (Gly, G), histidine (His, H), isoleucine (Ile, I), leucine (Leu, L), lysine (Lys, K), methionine (Met, M), phenylalanine (Phe, F), proline (Pro, P), serine (Ser, S), threonine (Thr, T), tryptophan (Trp, W), tyrosine (Tyr, Y), and valine (Val, V).

Furthermore, the amino acids of the X, Y, and Z component regions of the synthetic growth factor analogues of the invention can include any of the naturally occurring amino acids not found naturally in proteins, e.g., 3-alanine, betaine (N,N,N-trimethylglycine), homoserine, homocysteine, γ-amino butyric acid, ornithine, and citrulline.

Additionally, the amino acids of the X, Y, and Z component regions of the synthetic growth factor analogues of the invention can include any of the non-biological amino acids, i.e., those not normally found in living systems, such as for instance, a straight chain amino carboxylic acid not found in nature. Examples of straight chain amino carboxylic acids include 6-aminohexanoic acid, 7-aminoheptanoic acid, 9-aminononanoic acid, and the like.

For example Z may be selected from one of the following heparin binding sequences BBBxxB (SEQ ID NO 1), BxBB (SEQ ID NO 20) where each B is independently lysine, arginine, ornithine, or histidine and each x is independently a naturally occurring amino acid. Alternatively, Z may be RKRKLEGIAR (SEQ ID NO 2), RKRKLGRIAR (SEQ ID NO 3), RKRKLWRARA (SEQ ID NO 4), RKRLDRIAR (SEQ ID NO 5), RKRKLERIAR C (SEQ ID NO 6).

A synthetic growth factor analogue of one embodiment of the present invention, including those of Formulas I and II, provides that the X region is all or a portion, or a homolog of all or a portion, of any of the following amino acid sequences: AISMLYLDENEKVVL (SEQ ID NO: 7), ISMLYLDENEKVVLKNY (SEQ ID NO:6), LYFDESSNVILKK (SEQ ID NO:9), LYVDFSDVGWNDW (SEQ ID NO:10), EKVVLKNYQDMVVEG (SEQ ID NO:11), CAISMLYLDENEKVVL (SEQ ID NO:12), AFYCHGECPFPLADHL (SEQ ID NO:13), PFPLADHLNSTNHAIVQTLVNSV (SEQ ID NO:14), VLYFDDSSNVILKKK (SEQ ID NO 15), SIKVAVAAK (SEQ ID NO 16), YRSRKYSSWYVALKRK (SEQ ID NO 17), WFLLTMAAK (SEQ ID NO 18), or KWIQEYLEKK (SEQ ID NO 19). In a preferred embodiment, the X region is the amino acid sequence ISMLYLDENEKVVLKNY (SEQ ID NO: 8). More preferably, the X region is the amino acid sequence LYFDESSNVILKK (SEQ ID NO: 9). More preferably still, the X region is the amino acid sequence AISMLYLDENEKVVL (SEQ ID NO:7).

The osteoconductive material comprises at least one of the compounds selected from a calcium salt, a collagen, a hydroxyapatite, a ceramic, and also includes demineralized bone matrix or other allograft material.

The osteoconductive material can be formed as a granule, a gel, a putty, a powder, a block, or a combination thereof. In a more preferred embodiment, the synthetic BMP-2 compound is B2A2-K-NS.

In another embodiment, the calcium sulfate (CaS) of the osteoconductive material is less than about 80 wt % of the material. In a preferred embodiment the CaS is between about 30-80 wt % of the granule.

In yet another embodiment, the osteoconductive material contains inorganic material consisting of about 20-100 wt % HA and about 0-75 wt % TCP. In yet another embodiment, the osteoconductive material comprises CaS, PGA fibers, and PLG. PGA, PLA, and PLG are examples of synthetic polymers. In still another embodiment of the present invention, the osteoconductive material comprises silicate substituting a portion of the phosphate ions in the Hydroxyapatite lattice.

In another embodiment, the osteoconductive material comprises a natural polymer like collagen.

In another embodiment, the osteoconductive material comprises one or more compounds selected from allograft bone, natural polymers, and synthetic polymers.

In yet another embodiment, the osteoconductive materials is formed into granules, powders, gel, putty, or any combination thereof.

In still another embodiment, the osteoconductive material is used in combination with a load bearing device to treat bone lesions.

In a further embodiment, the load bearing device is selected from cages, wedges, rods, pedicle screws, vertebral body replacement, intervertebral body fusion device, and rings for bone fusion, for example a spine fusion.

In yet another embodiment, the method further comprises adding host bone chips (autograft) in combination with the osteoconductive material near the bone lesion. The autograft can be obtained from the iliac crest or from the 'local' area of surgery. For example, during lumbar spinal fusion surgery, the local bone can be obtained during a facetectomy and/or a laminectomy. The combined heparin binding growth factor coated on an osteoconductive material is combined with autograft and can be delivered to the site of spine fusion. The sites can be cervical or lumbar in nature. Furthermore, the surgical approaches can include PLF (posterolateral fusion), PLIF (posterior lumbar interbody fusion), TLIF (transforaminal lumbar interbody fusion), or others that are known to those skilled in the art. The methods can furthermore entail posterior fixation devices such as pedicle screws/rods and others that are known to those skilled in the art.

Another embodiment of the present invention comprises a method for treating bone lesions. The method comprises providing a synthetic BMP-2 analogue peptide that is an amplifier/co-activator of endogenous BMP-2 to an osteoconductive material such that it is coated or bound to that material. The osteoconductive material and associated analogue is implanted in a bone lesion with subsequent release from the osteoconductive material. The active form of the analogue peptide augments endogenous BMP-2 to treat a bone lesion.

In still another embodiment, releasing the synthetic growth factor analogue from the osteoconductive material is rate controlled by manipulating the composition of the osteoconductive material, manipulating the amino acid composition, concentrating the synthetic BMP-2 peptide attached to the osteoconductive material, and/or controlling the calcium concentration in the osteoconductive material.

Yet another embodiment of the present invention comprises a kit. The kit comprises a vial of lyophilized vial of synthetic growth factor analogue, and separately a container of osteoconductive, inorganic granules. The kit is used to formulate an implantable material by hydrating the analogue with saline or water and mixing the resultant solution with the granules, whereupon analogue becomes attached to the granule. After discarding the solution, the granules with the attached analogue is then delivered to the bony lesion.

The following table describes heparin binding growth factor analogues and their biological activity that could promote bone formation when releasably attached to an osteoconductive matrix.

TABLE 1

| Name | Host Sequence Related to | Sequence ID | Biological activity associated with bone formation |
| --- | --- | --- | --- |
| F2A | Basic FGF | SEQ ID 17 | Angiogenesis |
| B7A | Bone Morphogenetic Protein - 7 | SEQ ID NO 15 | Binding to the BMP-7 receptor; co-activation with BMP-2 as a heterodimer |
| B2A2-K-NS | Bone Morphogenetic Protein - 2 | SEQ ID NO 7 | Binding to the BMP-2 receptor; co-activation of endogenous BMP-2 |
| SD-2 | Stromal Derived Factor - 1 | SEQ ID NO 19 | Chemotaxis |
| LA-2 | Laminin | SEQ ID NO 16 | Increase cell attachment, promote chemotaxis and angiogenesis |
| VA5 | Vascular endothelial growth factor | SEQ ID NO 18 | Increases angiogenesis |

Embodiments of the present invention are further illustrated with the following examples.

Examples

Example 1: Comparative Binding of B2A2-K-NS to Osteoconductive Bone Replacement Graft from Different Sources An evaluation of several commercially available osteoconductive bone replacement grafts (BRGs) was performed to determine their binding and release characteristics of the BMP-2 amplifier/co-activator known as B2A2-K-NS.

First, the materials were placed into 0.9% saline and the pH recorded.

The next step was to determine whether the peptide was able to bind these BRGs. B2A2-K-NS (approximately 20 µg/ml) was incubated in one ml of 0.9% saline solution with 0.17 gram BRGs for 15 minutes. An ELISA assay was performed both on peptide solution without BRGs and the supernatant from the peptide+BRG. The difference between the peptide only reading and the supernatant from the peptide+BRG provided the amount of peptide bound.

The third step was to measure the amount of peptide released using the same ELISA assay. Briefly, the peptide bound BRGs were placed in 1 ml of 0.9% saline and the amount of peptide released was measured over a 72 hours period.

The data is summarized in the table below.

TABLE 2

| Composition | pH | Level of peptide binding | Peptide Released? |
|---|---|---|---|
| 100% HA | 6.6 | High | N/D |
| 100% HA with silicon substitutions | 10.0 | Intermediate | Yes |
| 75:25 (HA:TCP) | 7.5 | Intermediate | N/D |
| 65:35 (HA:TCP) | 7.3 | None | N/A |
| 60:40 (HA:TCP) | 8.8 | High | Yes |
| 60:40 (HA:TCP) | 6.3 | High | Yes |
| 20:80 (HA:TCP) | 6.5 | High | Yes |
| 100% b-TCP | 7.0 | None | N/A |
| Triphasic: HA, TCP, CaS (1% w/w) | 9.0 | High | Yes |
| Triphasic: HA, TCP, CaS (10% w/w) | 10.5 | High | No |
| PGA fibers+~9% CaS + PLG | 3.7 | High | No |

The binding definitions are defined as follows: None is no detectable binding. High is binding >20 μg peptide/cc graft material. Intermediate is less than 20 μg peptide/cc graft material, but above non-detectable binding. B2A2-K-N-S was found to bind to BRGs in the pH range of 3.7-10.5.

B2A2-K-NS was found to bind HA or HA/TCP containing BRGs ranging from 100% to 20% hydroxyapatite and from 80% to 25% tricalcium phosphate. B2A2-K-NS was found to bind HA/TCP/CaS BRG ranging from 0% to 10% calcium sulfate. B2A2-K-NS was found to bind a BRG that contains polyglycolic and polylactic acid combined with calcium sulfate.

A surprise finding was that materials that are similar in composition differ greatly in their ability to bind B2A2-K-NS. Whereas two 60:40 HA: TCP and one 75:25 HA: TCP BRGs were able to bind B2A2-K-NS, a 65:35 HA: TCP composition was unable to bind B2A2-K-NS.

The relative amounts of HA: TCP did not determine whether the peptide was released or not. For example, one 60:40 HA: TCP BRG released the peptide at "high" rates whereas the other 60:40 HA: TCP BRG released the peptide at "intermediate" rates. More importantly for release was the presence and quantity of CaS in the granule. B2A2-K-NS could not release from the biomaterial at acceptable levels at a CaS amount of ~9-10%, but could release at a CaS concentration of 1%.

B2A2-K-NS could release from the biomaterial at acceptable levels from materials ranging from 75% to 20% hydroxyapatite and 80% to 25% tricalcium phosphate. The peptide could release from materials in the pH range of 6.3-10.

Example 2: Binding of B2A2-K-NS to Ceramic Granules

Methods. 1.5 cc of granules were added to 1.8 mL of 0.9% saline or of peptide solution in 0.9% saline having a concentration of 35.9, 119.8, 359.3 μg/ml. The granule-peptide solutions were swirled vigorously for 15 seconds every 5 minutes for 20 minutes. After swirling, the supernatant was removed, filtered through 0.22 μm filter (low protein binding durapore (PVDF)) and assayed via Bicinchoninic Acid (BCA) or micro BCA assay (Pierce, Rockport, IL) for peptide content. The amount of peptide bound to the particles was obtained by subtraction method (the total peptide minus peptide present in the supernatant is equal to the amount of peptide bound on particulate materials.). The study was performed on two separate days and the results averaged below:

TABLE 3

| Granule | B2A2-K-NS concentration (ug/ml) | B2A2-K-NS bound (%) |
|---|---|---|
| 60:40 (pH 8.8) (HA:TCP) | 36 | 85 |
| 60:40 (pH 8.8) (HA:TCP) | 120 | 90 |
| 60:40 (pH 8.8) (HA:TCP) | 359 | 94 |
| 20:80 (HA:TCP) | 36 | 67 |
| 20:80 (MA:TCP) | 120 | 88 |
| 20:80 (HA:TCP) | 359 | 95 |
| 100% HA + silicon | 369 | 73 |
| 100% HA | 230 | 87 |

The study demonstrates that a high percentage of B2A2-K-NS peptide is bound on materials that include 100% hydroxyapatite and biphasic compositions comprised of 20:80 and 60:40 (HA: TCP).

Example 3: Release of B2A2-K-NS from Ceramic Granules

Methods: After binding the peptide to the granules as described in Example 2, each of the vials containing particulate materials was replenished with 1.8 mL of 0.9% saline and placed on the rocking platform. After specified time interval, the supernatant was removed, filtered, and collected over a period of 43 hrs. Based on the amount of the peptide present in the supernatant, the amount of peptide bound to or released from the particles as was calculated. The study was performed on two separate days with the averages plotted showing cumulative peptide released vs. time (see graph in FIG. 1) (Note: the HA plus silicon was only performed at high dose). A BCA assay was utilized to determine peptide concentrations. The 60:40 granule was pH 8.8.

Referring now to FIG. 1, the release characteristics of specified materials tested. There was a burst of peptide released over a 4 hour period (supernatant was assessed hourly for the first four hours). At high loading doses (431 µg peptide/cc granule), the burst phase accounted for 12-22% of the total amount of peptide loaded. For intermediate loading doses (144 µg peptide/cc granule), the burst phase accounted for 25-35% of the total amount loaded. For low doses (43 µg peptide/cc granule), the burst phase accounted for 48-59% of the total amount loaded. Following the burst period, there was a slower, sustained release period.

FIG. 1 illustrates similarly shaped B2A2-K-NS peptide release curves for granules consisting of 100% hydroxyapatite and biphasic compositions comprising 20:80 and 60:40 HA: TCP (pH 6.3).

The diamond on the graph represents 60% HAP and 40% TCP (high dose). The square represents 60% HAP and 40% TCP (medium dose). The triangle represents 20% HAP and 80% TCP (high dose). The X represents 20% HAP and 80% TCP (medium dose). The star represents 100% HAP plus Si (high dose). The filled-in circle represents 60% HAP and 40% TCP (low dose), and the plus sign represents 20% HAP and 80% TCP (low dose).

Figure 2:
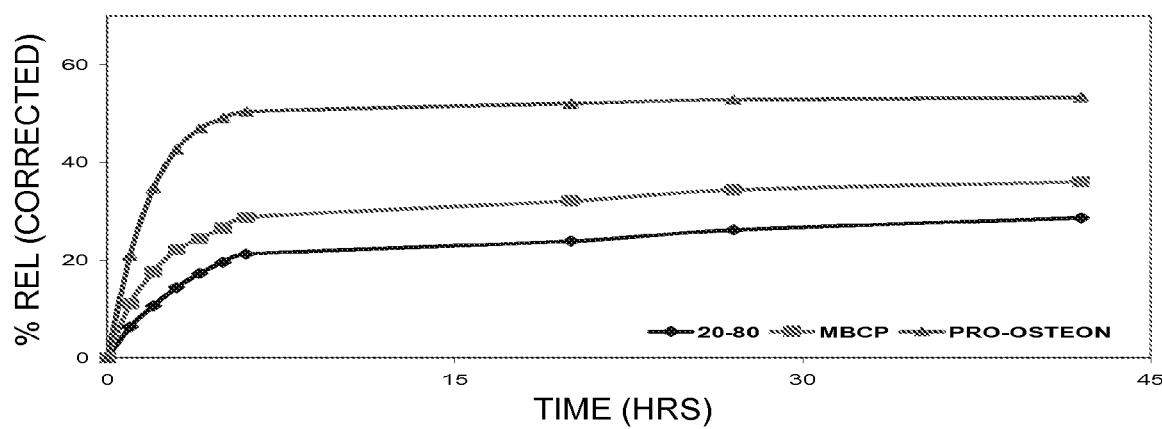
FIG. 2 illustrates B2A2-K-NS release from different osteoconductive materials.

Referring now to FIG. 2, the study was repeated using similar conditions as above using the high B2A2-K-NS dose. The granule size was 1-3 mm except for Pro-Osteon, which was ~0.5 mm. The bovine serum albumin (BSA) standard curve was generated using the supernatant from the granules (without peptide). The B2A2-K-NS BCA value was corrected relative to the BSA standard curve.

FIG. 2 illustrates similarly shaped B2A2-K-NS peptide release curves for granules consisting of 100% hydroxyapatite (Pro-Osteon) and biphasic compositions comprising 20:80 and 60:40 HA: TCP (MBCP).

To those skilled in the art, it should be recognized that, to reproduce these results, the same volume of supernatant and the same number of collection points listed above should be utilized. Increasing the supernatant volume or increasing the number of supernatant collections over a given time period will likely increase the observed amount of peptide released. Conversely, decreasing the supernatant volume or decreasing the number of supernatant collections over a given time period will likely decrease the observed amount of peptide released. In addition, modification of the supernatant solution from 0.9% saline to water or another solvent will likely alter the total quantity released. Omitting the supernatant filtration will increase the recovered amount of peptide and increasing the swirling rate may increase the amount of peptide released. Performing the BSA standard curve with supernatant released from the granules may decrease the peptide quantity observed.

Example 4: Efflux of B2A2-K-NS from Ceramic Granules

Figure 3:
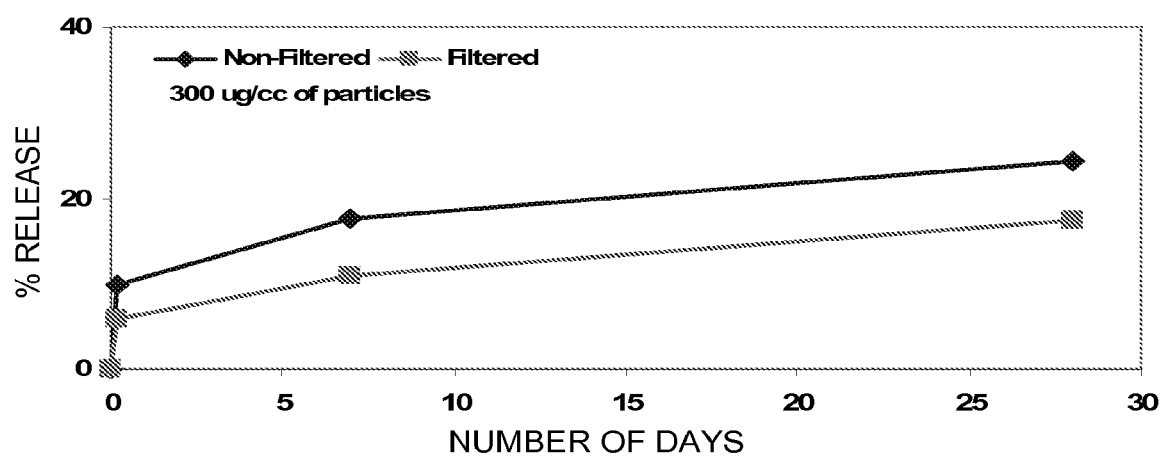
FIG. 3 illustrates B2A2-K-NS release over 28 days according to one embodiment of the present invention.

The experiment described in Example 3 was repeated using 20:80 granules coated with 300 µg B2A2-K-NS/ml granules. 3 cc granules were used; 3.6 ml of 0.9% saline was collected at the time points to determine peptide release. Referring now to FIG. 3, a long-term cumulative B2A2-K-NS release over a period of 28 days is illustrated. The two curves show the amount of peptide released after filtration (squares) or prior to filtration (diamonds) of the supernatant. A 0.22 µm filter (low protein binding durapore PVDF) was utilized.

Example 5: Method Used for Determination of Release of B2A2-K-NS from Granules

Peptide release from 20% HAP/80% TCP was determined using the following method. 1.5 cc of granules were added to 1.8 mL of 0.9% saline or of peptide solution in 0.9% saline having a concentration of 43, 143, or 431 µg B2A2-K-NS/cc granule. The granule-peptide solutions were swirled vigorously for 15 seconds every 5 minutes for 20 minutes. After swirling, the supernatant was removed and assayed via BCA or micro BCA assay for peptide content.

Figure 4:
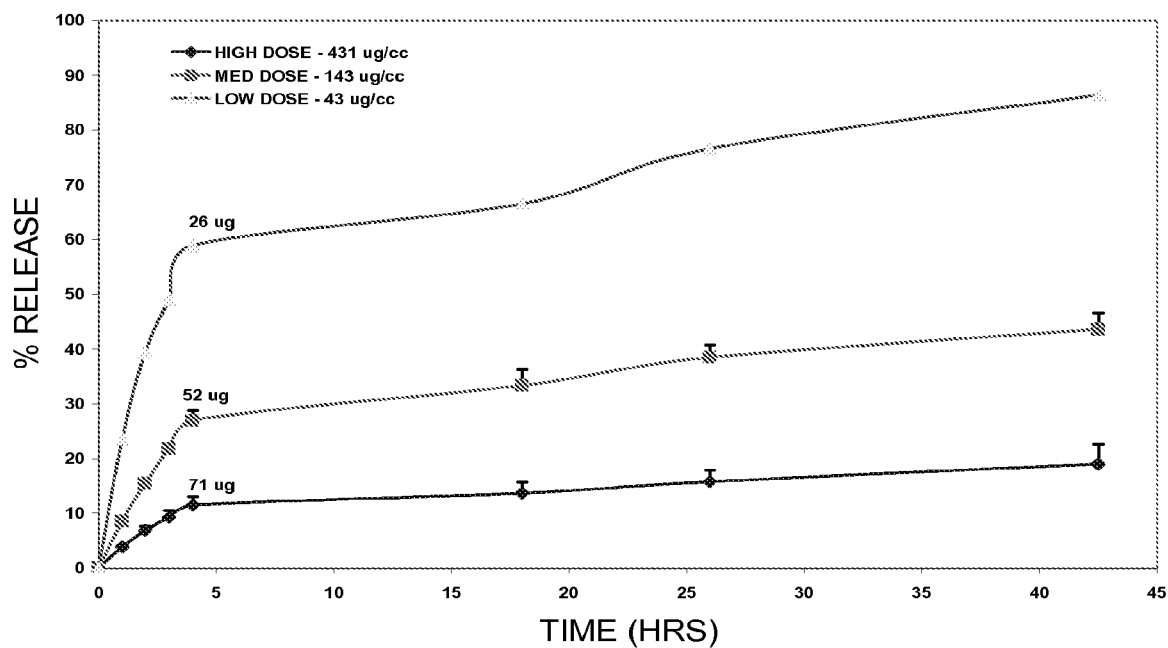
FIG. 4 illustrates B2A2-K-NS release at several concentrations from an osteoconductive material according to one embodiment of the present invention.

Referring now to FIG. 4, a similarly shaped release curve is generated for the same peptide at high dose (diamonds), medium dose (squares) and low dose (triangles) and illustrates that the peptide coating concentration affects the magnitude of the release.

Example 6: Comparative Binding of Synthetic Growth Factor Analogues to Ceramic Granules In order to better determine the physical characteristics of peptide binding and release, several peptides were compared on a single scaffold. Although the other peptides tested were not co-activators of BMP-2, they share a similar structure in that they are branched, of a similar size, and contain a heparin binding domain.

Methods for assaying peptide release from a single scaffold are as follows: 1 cc of granules were added to 1.2 mL of 0.9% saline or of peptide solution in 0.9% saline having a concentration of 100 µg B2A2-K-NS, LA2, or F2A4/cc granule. The granule-peptide solutions were swirled vigorously for 15 seconds every 5 minutes for 20 minutes. After swirling, the supernatant was removed and assayed via BCA or micro BCA assay for peptide content. The BCA value for each peptide was corrected relative to the BSA standard curve.

Figure 5:
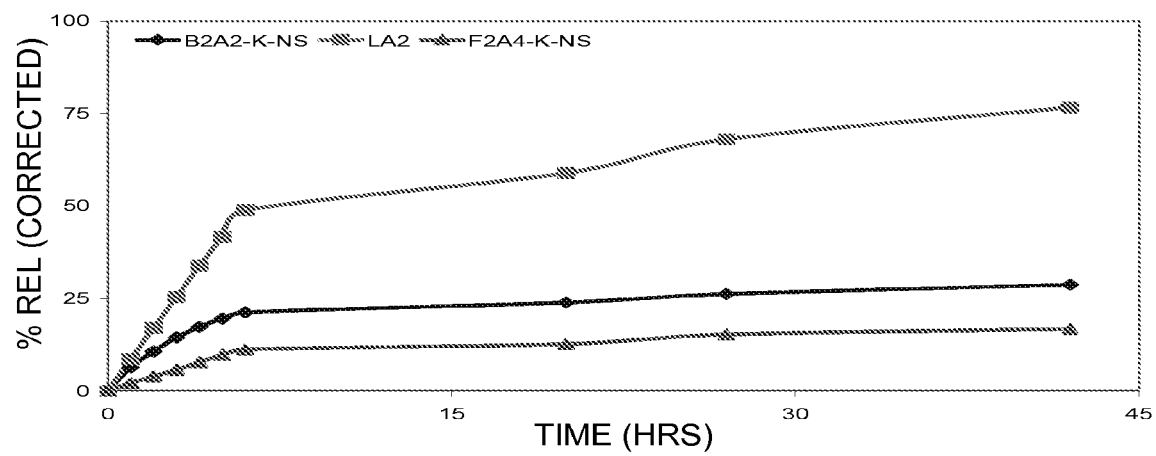
FIG. 5 illustrates three different peptides released from an osteoconductive material according to one embodiment of the present invention.

Referring now to FIG. 5, the shape of the release curve is similar for all three peptides (B2A2-K-NS (diamonds), LA2 (squares), and F2A4-K-NS (triangles)). However, the magnitude of the release is markedly different. The following table shows the amino acid composition of each peptide.

TABLE 4

| Peptide | + charges Incl. NH2 | − charges | Hydrophobic incl. Ahx | Aromatic | Length peptide | MW |
| --- | --- | --- | --- | --- | --- | --- |
| LA2 | 10 | 1 | 18 | 0 | 30 | 3272 |
| B2A2-K-NS | 11 | 7 | 20 | 2 | 45 | 5344 |
| F2A4 | 17 | 1 | 12 | 8 | 43 | 5540 |

The numbers of positive, negative, or hydrophobic amino acids for each peptide were similar and do not appear to account for the large differences in the observed release rates. Charge distribution of each peptide is illustrated in FIG. 6.

The charge distribution on the amino acid terminus is similar in all peptides and so this region would not be expected to contribute to the differences in release rates. One possible reason for why F2A4 does not release readily is the wide distribution of positive amino acids, which could interact with the negatively charged hydroxyapatite/TCP surface. The aromatic amino acids may help distribute the positive charges across a greater region of the peptide. The number of positive charges is not interrupted by any negative charges. In contrast, B2A2-K-NS has fewer positively charged groups and the positive charges are interrupted by negatively charged groups. The most rapidly released peptide, LA2, only has two amino acids at the very carboxyl terminus and these amino acids are bordered on one side by non-aromatic hydrophobic residues. The long region of non-aromatic hydrophobic domain located in the branched area of the peptide may also promote easy dislodging, as neither F2A4 or B2A2-K-NS has such an extensive hydrophobic region.

Example 7: Bioactivity of B2A2-K-NS Released from Ceramic Granules

Methods: (A) Peptide was collected over a six hour period after release from 20:80 (as described in Example 3). The supernatants from all time points were mixed, frozen, and lyophilized for 48 hours. The peptide pellet was reconstituted in 1.5 ml saline and a BCA assay performed to determine peptide concentration.

(B) Alkaline phosphatase assays were performed using mouse pluripotent cell lines C2C12. Cells were plated in 96-well ($1 \times 10^4$/well) plates in DMEM/F-12 Ham's containing 15% FBS, 1% L-gln, 1% NaPyr, and 1% gentamycin and allowed 24 hours to attach at 37 C, 5% $CO_2$, 90% humidity. The medium was then aspirated and replaced with a low-serum (5% FBS) medium containing B2A2-K-NS in various concentrations ranging from 1.25- to 10 µg/ml, with or without addition of BMP-2 (100 ng/ml). After 1 day, ALP activity was determined.

Results and conclusion: B2A2-K-NS peptide released from 20:80 increased BMP-2 activity, which demonstrated B2A2-K-NS activity after release from 20:80 granules.

Example 8: Binding of B2A2-K-NS to Collagen

Type I, bovine-derived, dermal collagen sheets that were crosslinked with DHT and lyophilized were incubated with 1,072 µg B2A2-K-NS/ml collagen sheet in 0.9% saline solution. The binding efficiency was 61%, which was far lower than the binding efficiency on the $Ca^{2+}$containing granules at high B2A2-K-NS coating concentrations (87-95% as described in Example 2). Lower binding efficiencies may be attributed to lower surface area as compared to that of the granules.

To initiate release, a vial containing collagen coated with B2A2-K-NS was replenished with 2 ml of 0.9% saline and placed on the rocking platform. After specified time interval, the supernatant was removed, filtered, and collected. A BCA assay was utilized to determine peptide concentrations. Hourly collections in 0.9% saline demonstrated that the cumulative amount of peptide released was 11, 19, 23, and 28% after 1, 2, 3, and 4 hours, respectively. The BSA standard curve was generated by placing BSA in supernatant from the collagen sponge (without peptide). The release rates from collagen were faster than the release rates from 20:80 using comparable conditions.

Example 9: Use of B2A2-K-NS/Ceramic Granules to Augment Posterolateral Spinal Fusion in Rabbits All procedures were approved by the Institutional Animal Care Use Committee. Skeletally mature New Zealand White Rabbits weighing 4.5-5.5 kg were individually caged and monitored daily for signs of pain and discomfort. All operative procedures were performed in a surgical suite using inhalation anesthesia and aseptic techniques. A pre-anesthetic dose of Ketamine HCl 2 6 mg/kg, Acepromazine Maleate 0.15 mg/kg, and Xylazine HCl 0.78 mg/kg was administered IM. Rabbits were masked and 1.5-2.5% isoflurane was delivered in $O_2$.

A single level posterolateral lumbar intertransverse process fusion (PLF) was performed in 60 rabbits, bilaterally at L4-L5, with autogenous bone graft from the iliac crest and differing doses of B2A2-K-NS. Rabbits were placed prone on the operating table and surgically prepped with 70% Betadine solution. A dorsal midline incision, approximately 15 centimeters long, was made from L1 to the sacrum and the soft-tissues overlying the transverse processes (TP) were dissected. The TPs were then decorticated with a high-speed burr.

The study consisted of the following materials (10 animals per treatment) placed between the transverse processes in the paraspinal bed (3 ml per side); the autograft group (consisting of morselized, cancellous bone graft); the open group (no graft material); the granule only group (no B2A2-K-NS coating concentration) (B2A2-K-NS/G 0 µg); the low coating concentration treated granule group (B2A2-K-NS/G 50 µg), the medium coating concentration treated granule group (B2A2-K-NS/G 100 µg) and the high coating concentration treated granule group (B2A2-K-NS/G 300 µg). All animals treated with granules contained approximately 50% autograft by volume. The granule used was 20:80 (HA:TCP).

Fascia and skin were closed with 3-0 Vicryl and then the skin was stapled. Cephalothin (13 mg/kg) was administered prior to surgery and twice a day for 5 days postoperatively. To insure the animals were comfortable, analgesics are administered based on the observation of the PI. Butorphanol (1-7.5 mg/kg IM q4) and Flunixin Meglumine (1.1 mg/kg IM q12) were given daily for 48 hours post-op. Euthanasia was performed at six weeks followed by radiographs and manual palpation by three blinded examiners to determine fusion. If one side was deemed fused by two out of three examiners then the spine was determined fused. All surgeons were also blinded to the treatment at the time of surgery. Fusion was also assessed via examination of radiographic plain films.

TABLE 5

| Treatment | Manual Palpation fusion rate (%) | Radiographic fusion rate (%) |
|---|---|---|
| Open | 0 | 0 |
| Autograft - positive control | 63 | 55 |
| B2A2-K-NS/G 0 | 33 | 66 |
| B2A2-K-NS/G 50 | 78 | 88 |
| B2A2-K-NS/G 100 | 89 | 89 |
| B2A2-K-NS/G 300 | 80 | 80 |

The fusion rate for graft material augmented with each B2A2-K-NS dose was clearly higher than the autograft fusion rate.

The results clearly demonstrate that the B2A2-K-NS delivery kinetics and quantities are optimized to match the amount of host BMP-2 and to enhance its activity in this bony repair indication.

Example 10: Excipients Added to the Peptide as Bulking Agents

Excipients were added to the peptide as bulking agents, stabilizers, to prevent non-specific binding, etc. These excipients which did not interfere with peptide binding to the granules include the following:
(1) 0.9% saline (no excipients)
(2) 5.5% dextrose
(3) 5.5% dextrose+0.05% Tween 20
(4) 2% mannitol+0.1% dextrose+0.05% polysorbate 80
(5) 5.5% dextrose (6) 4% mannitol+10 mM glycine The resulting formulations were bound to 60:40 (HA: TCP) (pH 8.8) and 20:80 (HA: TCP) granules. All excipient containing formulations resulted in improved peptide binding to both materials as monitored by HPLC or colorimetric techniques as compared to formulations, which lacked excipients.

Example 11: Use of B2A2-K-NS/Ceramic Granules to Augment Instrumented Interbody Spinal Fusion in Sheep B2A2-K-NS/ceramic granules (B2A2-K-NS/G) with or without 1:1 v/v morselized ilicac crest bone where surgically implanted in the lumbar spines of sheep at L2-L3 and L4-L5 in Tetris® PEEK cages (Signus Medical, LLC). 100% morselized cancellous iliac autograft was used as a positive control material. For the experimental treatments, 50% of the appropriate treatment device and 50% morselized iliac cancellous graft were implanted. Treatments were performed according to a pre-defined randomization table and strictly according to the cage manufacturer's recommendations for device implantation. Morselized cancellous iliac crest was used for all autograft treatments (positive control). After fluoroscopic verification of the previously implanted cage, the two operative levels (L2-L3 and L4-L5) were then instrumented with the Silhouette™ polyaxial pedicle screw and rod system (Zimmer Spine, Inc.) using standard technique for pedicle preparation and screw placement. For wound closures, the muscle, subcutaneous layer, and skin were approximated with running and interrupted 1-0 Vicryl sutures and the skin closed with staples.

At four months for the B2A2-K-NS/G autograft group and six months for the B2A2-K-NS/G lacking autograft group, the animals were sacrificed and the following analyses were performed. Non-destructive biomechanical testing evaluated fusion of the motion segment, CT evaluated fusion within the cage and between the two endplates. Additionally, the quality of bone formed within the VBR (which may be protected from stresses) was assessed by destructive biomechanical testing.

The following definitions for fusion were utilized:

CT=At least two sagittal slices on the CT images demonstrated evidence of contiguous bone from endplate to endplate without sines of radiolucencies. Two of three blinded examiners had to agree on the fusion status.

Non-destructive biomechanical testing=<3° motion in flexion-extension

The following results are for B2A2-K-NS/G that was mixed 1:1 with autograft after 4 months.

TABLE 6

| Treatment | Fusion rate by CT (%) | Fusion rate by non-destructive biomechanical testing |
|---|---|---|
| Autograft | 100 | 88 |
| B2A2-K-NS/G 0 ug | 63 | 88 |
| B2A2-K-NS/G 50 ug | 88 | 88 |
| B2A2-K-NS/G 100 ug | 88 | 100 |
| B2A2-K-NS/G 300 ug | 88 | 75 |
| B2A2-K-NS/G 600 ug | 75 | 88 |

The destructive testing demonstrated statistically comparable results among all treatments tested (autograft, B2A2-K-NS/G 0 µg, B2A2-K-NS/G 50 µg, and B2A2-K-NS/G 100 µg) which indicated comparable bone quality among all groups. For B2A2-K-NS/G 100 µg that did not contain autograft after 6 months, the fusion rate was 86% by CT and 100% by non-destructive biomechanical testing.

The fusion rate for graft material augmented with B2A2-K-NS 2-K-NS dose (50-300) was comparable to the autograft fusion rate and higher than the graft material without the B2A2-K-NS coating. The results clearly demonstrate that the B2A2-K-NS delivery kinetics and quantities are optimized to match the amount of host BMP-2 and to enhance its activity in this bony repair indication.

Example 12: Use of B2A2-K-NS Granules with Exogenous Recombinant BMP-2 to Induce Ectopic Bone Sterile ceramic granules (Berkeley Advanced Biomaterials, Inc.; 60:40 (HA: TCP)) where coated by immersing them for 30 minutes in a solution containing B2A2-K-NS (0-, 2.5-, 10-, 25 µg/ml). Thereafter, the solution was removed by aspiration and the granules allowed to air dry. The coated granules were then placed in sterile gelatin capsules. Immediately before subcutaneous implant in rats, the capsules were injected with a collagen-based gel (GFR-Matrigel) containing 1 µg recombinant BMP-2. The capsules were placed subcutaneously in young adult rats on the flanks in pre-prepared pouches and the surgical site closed with surgical clips. After 30 days, the implants were surgically removed, weighed, and palpated to assess hardness. The explants were then fixed with multiple changes into 70% ethanol. The explants coated with 25 µg B2A2-K-NS had a significantly higher weight than controls (no BMP-2, no B2A2-K-NS), and tended (p=0.11) to have a higher weight than those containing BMP-2 but no B2A2-K-NS. All implants coated with 25 µg B2A2-K-NS were judged to be palpably hardened (4/4), whereas implants containing BMP-2 but no B2A2-K-NS had less hardening (1/4). Implants coated with 2.5 or 10 µg B2A2-K-NS were intermediate (3/4). Histological examination of the implants following staining with hematoxylin and eosin revealed new bone formation consistent with the palpation results. All implants coated with 25 µg B2A2-K-NS had histologically identifiable new bone (4/4), whereas implants containing BMP-2 but no B2A2-K-NS had less (1/4).

The present invention has been described in terms of preferred embodiments. However, it will be appreciated that various modifications and improvements may be made to the described embodiments without departing from the scope of the invention. Variations and modifications of the present invention will be obvious to those skilled in the art and is intended to cover in the appended claims all such modifications and equivalents. The entire disclosures of all references, applications, patents, and publications cited above are hereby incorporated by reference.

What is claimed is:

1. A composition comprising:
    a synthetic growth factor analogue selected from:
    VLYFDDSSNVILKKK (VLYFDDSSNVILKK) HxHxHxRKRKLERIAR-amide (B7A), WFLLTMAAK (WFLLTMAA) HxHxHxRKRKLERIAR-amide (VA5), and KWIQEYLEKK (KWIQEYLEK) HxHxHxRKRKLERIAR-amide (SD-2),
    wherein Hx is aminohexanoic acid; and
    an osteoconductive material comprising one or more selected from an inorganic material, a synthetic polymer, a natural polymer, and an allograft bone;
    wherein the synthetic growth factor analogue is releasably attached to the osteoconductive material.

2. The composition of claim 1, wherein the synthetic growth factor analogue is B7A.

3. The composition of claim 1, wherein the synthetic growth factor analogue is VA5.

4. The composition of claim 1, wherein the synthetic growth factor analogue is SD-2.

5. The composition of claim 1, wherein the synthetic growth factor analogue modulates the response to bone morphogenetic proteins.

6. The composition of claim 1, wherein the synthetic growth factor analogue modulates the osteoinductive environment by amplifying or co-activating cell growth, chemotaxis, or cell attachment.

7. The composition of claim 1, wherein the osteoconductive material comprises one or more selected from hydroxyapatite, tricalcium phosphate, collagen, hyaluronate, calcium sulfate, polyglycolic acid fibers, polylactic-co-glycolic acid, and allograft bone.

8. The composition of claim 1, wherein the osteoconductive material comprises a calcium sulfate salt.

9. The composition of claim 8, wherein the osteoconductive material comprises about 30-80 wt % calcium sulfate.

10. The composition of claim 1, wherein the osteoconductive material comprises one or both of hydroxyapatite and tricalcium phosphate.

11. The composition of claim 1, wherein the osteoconductive material contains about 20 wt % hydroxyapatite and about 80 wt % tricalcium phosphate.

12. The composition of claim 1, wherein the osteoconductive material comprises a hydroxyapatite comprising silicate substituting a portion of the hydroxyapatite phosphate ions.

13. The composition of claim 1, wherein the osteoconductive material is in a form selected from a granule, a putty, a powder, a gel, a block, and combinations thereof.

14. The composition of claim 1, wherein the composition further comprises one or more excipients selected from mannitol and glycine.

15. A kit comprising:
a vial containing a lyophilized synthetic growth factor analogue selected from:
VLYFDDSSNVILKKK (VLYFDDSSNVILKK) HxHxHxRKRKLERIAR-amide (B7A), WFLLTMAAK (WFLLTMAA) HxHxHxRKRKLERIAR-amide (VA5), and KWIQEYLEKK (KWIQEYLEK) HxHxHxRKRKLERIAR-amide (SD-2),
wherein Hx is aminohexanoic acid; and
a container containing an osteoconductive material.

16. A method for treating a bone lesion in a subject comprising implanting the composition of claim 1 into the bone lesion.

17. The method of claim 16, further comprising implanting an exogenous or recombinant bone growth factor.

18. The method of claim 16, wherein the osteoconductive material comprises one or more selected from hydroxyapatite, tricalcium phosphate, collagen, hyaluronate, calcium sulfate, polyglycolic acid fibers, polylactic-co-glycolic acid, and allograft bone.

19. The method of claim 16, wherein the osteoconductive material is formed from granules, polymers, powders, gel, cement, putty, or any combination thereof.

\* \* \* \* \*

SEQUENCE LISTING

<160> NUMBER OF SEQ ID NOS: 20

<210> SEQ ID NO 1
<211> LENGTH: 6
<212> TYPE: PRT
<213> ORGANISM: Artificial
<220> FEATURE:
<223> OTHER INFORMATION: Heparin-Binding Motif
<220> FEATURE:
<221> NAME/KEY: 1
<222> LOCATION: (1)..(3)
<223> OTHER INFORMATION: where each Xaa is independently lysine,
      arginine, ornithine, or histidine
<220> FEATURE:
<221> NAME/KEY: 1
<222> LOCATION: (4)..(5)
<223> OTHER INFORMATION: where each Xaa is indenpendently a naturally
      occuring amino acid
<220> FEATURE:
<221> NAME/KEY: 1
<222> LOCATION: (6)..(6)
<223> OTHER INFORMATION: where Xaa is lysine, arginine, orniithine or
      histidine

<400> SEQUENCE: 1

Xaa Xaa Xaa Xaa Xaa Xaa
1               5

<210> SEQ ID NO 2
<211> LENGTH: 10
<212> TYPE: PRT
<213> ORGANISM: Artificial
<220> FEATURE:
<223> OTHER INFORMATION: Heparin-Binding Motif

<400> SEQUENCE: 2

Arg Lys Arg Lys Leu Glu Gly Ile Ala Arg
1               5                   10

<210> SEQ ID NO 3
<211> LENGTH: 10
<212> TYPE: PRT
<213> ORGANISM: Artificial
<220> FEATURE:
<223> OTHER INFORMATION: Heparin-Binding Motif

<400> SEQUENCE: 3

Arg Lys Arg Lys Leu Gly Arg Ile Ala Arg
1               5                   10

<210> SEQ ID NO 4
<211> LENGTH: 10
<212> TYPE: PRT
<213> ORGANISM: Artificial
<220> FEATURE:
<223> OTHER INFORMATION: Heparin-Binding Motif

<400> SEQUENCE: 4

Arg Lys Arg Lys Leu Trp Arg Ala Arg Ala
1               5                   10

<210> SEQ ID NO 5
<211> LENGTH: 9
<212> TYPE: PRT
<213> ORGANISM: Artificial
<220> FEATURE:
<223> OTHER INFORMATION: Heparin-Binding Motif

<400> SEQUENCE: 5

```
Arg Lys Arg Leu Asp Arg Ile Ala Arg
1               5

<210> SEQ ID NO 6
<211> LENGTH: 11
<212> TYPE: PRT
<213> ORGANISM: Artificial
<220> FEATURE:
<223> OTHER INFORMATION: Heparin-Binding Motif

<400> SEQUENCE: 6

Arg Lys Arg Lys Leu Glu Arg Ile Ala Arg Cys
1               5                   10

<210> SEQ ID NO 7
<211> LENGTH: 15
<212> TYPE: PRT
<213> ORGANISM: artificial
<220> FEATURE:
<223> OTHER INFORMATION: Bone Morphogenic Protein analogue

<400> SEQUENCE: 7

Ala Ile Ser Met Leu Tyr Leu Asp Glu Asn Glu Lys Val Val Leu
1               5                   10                  15

<210> SEQ ID NO 8
<211> LENGTH: 17
<212> TYPE: PRT
<213> ORGANISM: Artificial
<220> FEATURE:
<223> OTHER INFORMATION: Bone Morphogenic Protein analogue

<400> SEQUENCE: 8

Ile Ser Met Leu Tyr Leu Asp Glu Asn Glu Lys Val Val Leu Lys Asn
1               5                   10                  15

Tyr

<210> SEQ ID NO 9
<211> LENGTH: 13
<212> TYPE: PRT
<213> ORGANISM: Artificial
<220> FEATURE:
<223> OTHER INFORMATION: Bone Morphogenic Protein analogue

<400> SEQUENCE: 9

Leu Tyr Phe Asp Glu Ser Ser Asn Val Ile Leu Lys Lys
1               5                   10

<210> SEQ ID NO 10
<211> LENGTH: 13
<212> TYPE: PRT
<213> ORGANISM: Artificial
<220> FEATURE:
<223> OTHER INFORMATION: Bone Morphogenic Protein analogue

<400> SEQUENCE: 10

Leu Tyr Val Asp Phe Ser Asp Val Gly Trp Asn Asp Trp
1               5                   10

<210> SEQ ID NO 11
<211> LENGTH: 15
<212> TYPE: PRT
<213> ORGANISM: Artificial
<220> FEATURE:
<223> OTHER INFORMATION: Bone Morphogenic Protein analogue

<400> SEQUENCE: 11
```

```
Glu Lys Val Val Leu Lys Asn Tyr Gln Asp Met Val Val Glu Gly
1               5                   10                  15

<210> SEQ ID NO 12
<211> LENGTH: 16
<212> TYPE: PRT
<213> ORGANISM: Artificial
<220> FEATURE:
<223> OTHER INFORMATION: Bone Morphogenic Protein analogue

<400> SEQUENCE: 12

Cys Ala Ile Ser Met Leu Tyr Leu Asp Glu Asn Glu Lys Val Val Leu
1               5                   10                  15

<210> SEQ ID NO 13
<211> LENGTH: 16
<212> TYPE: PRT
<213> ORGANISM: Artificial
<220> FEATURE:
<223> OTHER INFORMATION: Bone Morphogenic Protein

<400> SEQUENCE: 13

Ala Phe Tyr Cys His Gly Glu Cys Pro Phe Pro Leu Ala Asp His Leu
1               5                   10                  15

<210> SEQ ID NO 14
<211> LENGTH: 23
<212> TYPE: PRT
<213> ORGANISM: Artificial
<220> FEATURE:
<223> OTHER INFORMATION: Bone Morphogenic Protein

<400> SEQUENCE: 14

Pro Phe Pro Leu Ala Asp His Leu Asn Ser Thr Asn His Ala Ile Val
1               5                   10                  15

Gln Thr Leu Val Asn Ser Val
            20

<210> SEQ ID NO 15
<211> LENGTH: 15
<212> TYPE: PRT
<213> ORGANISM: Artificial
<220> FEATURE:
<223> OTHER INFORMATION: Bone Morphogenic Protein 7 analogue

<400> SEQUENCE: 15

Val Leu Tyr Phe Asp Asp Ser Ser Asn Val Ile Leu Lys Lys Lys
1               5                   10                  15

<210> SEQ ID NO 16
<211> LENGTH: 9
<212> TYPE: PRT
<213> ORGANISM: Artificial
<220> FEATURE:
<223> OTHER INFORMATION: Laminin analogue

<400> SEQUENCE: 16

Ser Ile Lys Val Ala Val Ala Ala Lys
1               5

<210> SEQ ID NO 17
<211> LENGTH: 16
<212> TYPE: PRT
<213> ORGANISM: Artificial
<220> FEATURE:
<223> OTHER INFORMATION: FGF analogue
```

```
<400> SEQUENCE: 17

Tyr Arg Ser Arg Lys Tyr Ser Ser Trp Tyr Val Ala Leu Lys Arg Lys
1               5                   10                  15

<210> SEQ ID NO 18
<211> LENGTH: 9
<212> TYPE: PRT
<213> ORGANISM: Artificial
<220> FEATURE:
<223> OTHER INFORMATION: Vascular endothelial growth factor

<400> SEQUENCE: 18

Trp Phe Leu Leu Thr Met Ala Ala Lys
1               5

<210> SEQ ID NO 19
<211> LENGTH: 10
<212> TYPE: PRT
<213> ORGANISM: Artificial
<220> FEATURE:
<223> OTHER INFORMATION: Stromal Derived Growth Factor analogue

<400> SEQUENCE: 19

Lys Trp Ile Gln Glu Tyr Leu Glu Lys Lys
1               5                   10

<210> SEQ ID NO 20
<211> LENGTH: 4
<212> TYPE: PRT
<213> ORGANISM: Artificial
<220> FEATURE:
<223> OTHER INFORMATION: Heparin-Binding Motif
<220> FEATURE:
<221> NAME/KEY: 20
<222> LOCATION: (1)..(1)
<223> OTHER INFORMATION: where  Xaa is independently lysine, arginine,
      ornithine, or histidine
<220> FEATURE:
<221> NAME/KEY: 20
<222> LOCATION: (2)..(2)
<223> OTHER INFORMATION: where Xaa is independently a naturally
      occurring amino acid
<220> FEATURE:
<221> NAME/KEY: 20
<222> LOCATION: (3)..(4)
<223> OTHER INFORMATION: where Xaa is independently arginine, ornithine,
      lysine or histidine

<400> SEQUENCE: 20

Xaa Xaa Xaa Xaa
1
```